(12) United States Patent
Vitek et al.

(10) Patent No.: US 8,623,601 B2
(45) Date of Patent: Jan. 7, 2014

(54) METHODS OF DIAGNOSING CANCER

(75) Inventors: Michael P. Vitek, Cary, NC (US); Dale J. Christensen, Cary, NC (US); J. Brice Weinberg, Durham, NC (US)

(73) Assignees: Cognosci, Inc., Research Triangle Park, NC (US); Duke University, Durham, NC (US)

( * ) Notice: Subject to any disclaimer, the term of this patent is extended or adjusted under 35 U.S.C. 154(b) by 0 days.

(21) Appl. No.: 13/549,387

(22) Filed: Jul. 13, 2012

(65) Prior Publication Data

US 2013/0018001 A1 Jan. 17, 2013

Related U.S. Application Data

(60) Provisional application No. 61/507,493, filed on Jul. 13, 2011.

(51) Int. Cl.
*C12Q 1/68* (2006.01)
*G01N 33/53* (2006.01)

(52) U.S. Cl.
USPC .......................................... 435/6.1; 435/7.1

(58) Field of Classification Search
None
See application file for complete search history.

(56) References Cited

U.S. PATENT DOCUMENTS

| | | |
|---|---|---|
| 2005/0047996 A1 | 3/2005 | Vogelstein et al. |
| 2010/0144627 A1 | 6/2010 | Vitek et al. |
| 2011/0166079 A1 | 7/2011 | Vitek et al. |
| 2013/0005645 A1 | 1/2013 | Vitek et al. |

FOREIGN PATENT DOCUMENTS

| | | |
|---|---|---|
| WO | WO 2010/019921 A2 | 2/2010 |
| WO | WO 2010/125566 A2 | 11/2010 |

OTHER PUBLICATIONS

Tockman et al (Cancer Res., 1992, 52:2711s-2718s).*
Alberts et al. (Molecular Biology of the Cell, 3rd edition, 1994, p. 465).*
Greenbaum et al. (Genome Biology, 2003, vol. 4, Issue 9, pp. 117.1-117.8).*
Trotta et al., GenBank Accession No. NM_001122821.1; *Homo sapiens* SET nuclear oncogene (SET), transcript variant 1, mRNA; May 21, 2011.
Trotta et al., GenBank Accession NM_003011.3. *Homo sapiens* SET nuclear oncogene (SET), transcript variant 2, mRNA; Mar. 21, 2011.
UniProt Accession Q01105/Q6FHZ5. SET Human; May 31, 2011.
Young, International Search Report and Written Opinion for International Application No. PCT/US2012/046792, mailed Dec. 28, 2012 (11 pages).

* cited by examiner

*Primary Examiner* — Sean Aeder
(74) *Attorney, Agent, or Firm* — Cooley LLP

(57) ABSTRACT

Provided are methods of predicting or assessing the level of severity of cancer or cancer progression in a patient comprising measuring levels of SET expression in a biological sample from a patient and comparing levels of SET expression to a control sample or standard value. Methods for predicting or evaluating the efficacy of a SET therapeutic and kits comprising at least one reagent for measuring SET protein expression are also provided.

19 Claims, 26 Drawing Sheets

SEQUENCE LISTING

```
<160> NUMBER OF SEQ ID NOS: 13

<210> SEQ ID NO 1
<211> LENGTH: 50
<212> TYPE: PRT
<213> ORGANISM: Homo sapiens

<400> SEQUENCE: 1

Met Ala Pro Lys Arg Gln Ser Pro Leu Pro Pro Gln Lys Lys Lys Pro
1               5                   10                  15

Arg Pro Pro Pro Ala Leu Gly Pro Glu Glu Thr Ser Ala Ser Ala Gly
            20                  25                  30

Leu Pro Lys Lys Gly Glu Lys Glu Gln Gln Glu Ala Ile Glu His Ile
        35                  40                  45

Asp Glu
    50

<210> SEQ ID NO 2
<211> LENGTH: 18
<212> TYPE: PRT
<213> ORGANISM: Homo sapiens

<400> SEQUENCE: 2

Met Ala Pro Lys Arg Gln Ser Pro Leu Pro Pro Gln Lys Lys Lys Pro
1               5                   10                  15

Arg Pro

<210> SEQ ID NO 3
<211> LENGTH: 37
<212> TYPE: PRT
<213> ORGANISM: Homo sapiens

<400> SEQUENCE: 3

Met Ser Ala Pro Ala Ala Lys Val Ser Lys Lys Glu Leu Asn Ser Asn
1               5                   10                  15

His Asp Gly Ala Asp Glu Thr Ser Glu Lys Glu Gln Gln Glu Ala Ile
            20                  25                  30

Glu His Ile Asp Glu
        35
```

```
<210> SEQ ID NO 4
<211> LENGTH: 14
<212> TYPE: PRT
<213> ORGANISM: Homo sapiens

<400> SEQUENCE: 4

Lys Glu Leu Asn Ser Asn His Asp Gly Ala Asp Glu Thr Ser
1               5                   10

<210> SEQ ID NO 5
<211> LENGTH: 24
<212> TYPE: DNA
<213> ORGANISM: Artificial Sequence
<220> FEATURE:
<223> OTHER INFORMATION: SET-1alpha f primer

<400> SEQUENCE: 5
agaagaaacc aagaccacct cctg                                          24

<210> SEQ ID NO 6
<211> LENGTH: 24
<212> TYPE: DNA
<213> ORGANISM: Artificial Sequence
<220> FEATURE:
<223> OTHER INFORMATION: SET-1alpha b primer

<400> SEQUENCE: 6
gtgttcaatc gcttcttgct gttc                                          24

<210> SEQ ID NO 7
<211> LENGTH: 26
<212> TYPE: DNA
<213> ORGANISM: Artificial Sequence
<220> FEATURE:
<223> OTHER INFORMATION: SET-1alpha probe
<220> FEATURE:
<221> NAME/KEY: misc_feature
<222> LOCATION: (1)..(26)
<223> OTHER INFORMATION: May be labeled with 4,5-dichloro-dimethoxy-
      fluorescein (JOE)

<400> SEQUENCE: 7
tgcaggcttg ccgaagaagg gagaaa                                        26

<210> SEQ ID NO 8
<211> LENGTH: 20
<212> TYPE: DNA
<213> ORGANISM: Artificial Sequence
<220> FEATURE:
<223> OTHER INFORMATION: SET-1beta f primer

<400> SEQUENCE: 8
cggcggccaa agtcagtaaa                                               20

<210> SEQ ID NO 9
<211> LENGTH: 24
<212> TYPE: DNA
<213> ORGANISM: Artificial Sequence
<220> FEATURE:
<223> OTHER INFORMATION: SET-1beta b primer

<400> SEQUENCE: 9
gtgttcaatc gcttcttgct gttc                                          24

<210> SEQ ID NO 10
<211> LENGTH: 25
<212> TYPE: DNA
<213> ORGANISM: Artificial Sequence
```

```
<220> FEATURE:
<223> OTHER INFORMATION: SET-1beta probe
<220> FEATURE:
<221> NAME/KEY: misc_feature
<222> LOCATION: (1)..(25)
<223> OTHER INFORMATION: May be labeled with carboxyfluorescein (FAM)

<400> SEQUENCE: 10
aaggagctca actccaacca cgacg                                            25

<210> SEQ ID NO 11
<211> LENGTH: 24
<212> TYPE: DNA
<213> ORGANISM: Artificial Sequence
<220> FEATURE:
<223> OTHER INFORMATION: SET-1common f primer

<400> SEQUENCE: 11
ccatcttcga agtccaccga aatc                                             24

<210> SEQ ID NO 12
<211> LENGTH: 22
<212> TYPE: DNA
<213> ORGANISM: Artificial Sequence
<220> FEATURE:
<223> OTHER INFORMATION: SET-1common b primer

<400> SEQUENCE: 12
gcctcttcct gctggcttta tt                                               22

<210> SEQ ID NO 13
<211> LENGTH: 30
<212> TYPE: DNA
<213> ORGANISM: Artificial Sequence
<220> FEATURE:
<223> OTHER INFORMATION: SET-1common probe
<220> FEATURE:
<221> NAME/KEY: misc_feature
<222> LOCATION: (1)..(30)
<223> OTHER INFORMATION: May be labeled with carboxyfluorescein (FAM)

<400> SEQUENCE: 13
ggatttgacg aaacgttcga gtcaaacgca                                       30
```

METHODS OF DIAGNOSING CANCER

CROSS REFERENCE TO RELATED APPLICATIONS

This application claims priority to U.S. Provisional Patent Application 61/507,493, filed on Jul. 13, 2011, the entire contents of which are incorporated herein by reference.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: COGO_025_01US_SeqList_ST25.txt, date recorded: Jul. 13, 2012, file size 4 kilobytes).

FIELD OF THE INVENTION

The invention relates generally to the field of cancer diagnosis and treatment. More specifically, the invention relates to novel methods of assessing the level of severity of cancer or the progression of cancer. The novel methods relate to measuring the level of SET expression in biological samples.

BACKGROUND OF THE INVENTION

Cancer is a class of diseases in which a group of cells exhibit uncontrolled growth, invasion and destruction of adjacent tissues, and metastasis (the spread of aberrant cells to other locations in the body), or in which cells fail to undergo programmed cell death (e.g. apoptosis) at the appropriate time. Cancer causes about 13% of all deaths worldwide. Current treatments for cancer depend upon the specific type of cancer and tissue involved, but include surgery, chemotherapy, radiation therapy, immunotherapy, and monoclonal antibody therapy among other methods. Although these treatment methods have been successful in some cases, they are hindered by adverse side effects or limited efficacy. For example, the efficacy of eliminating cancerous tissue by surgical removal of tumors is often limited by the tendency of cancers to invade adjacent tissue and metastasize to other sites in the body. Chemotherapy, as well as radiation treatment, is often limited by toxicity or damage to other tissues in the body. Thus, cancer remains a major health concern and there is a need for improved methods of diagnosing and treating cancer.

Diagnosis of cancer can occur at any stage of disease. In many cases, determination of an appropriate course of treatment, which may include invasive surgery or administration of toxic drugs, is postponed until disease progression is observed so that the severity of disease can be determined and the appropriate therapeutic course can be selected. Systems that would allow clinicians to rapidly determine whether a patient would benefit from aggressive treatment or whether a less aggressive form of treatment is appropriate would drastically improve the treatment of individuals with cancer.

Of the nearly 84,000 annual cases of leukemia in the Western world, B-cell CLL is the most common, accounting for ~30% of adult leukemia cases. (Ishibe el al. 2001) Characterized by accumulation of monoclonal mature B cells (Rozman et al. 1995), the CLL clinical course is heterogeneous, with some patients experiencing an aggressive course that demands early treatment, and others experiencing long survival without disease-related symptoms or ever requiring treatment. (Rozman et al. 1995) Aberrant apoptosis in CLL cells correlates with arrest either in the G0 or early G1 phases of the cell cycle. (Cordone et al. 1992) (Caligaris-Cappio et al. 1999) This defective apoptosis in CLL cells is partly due to aberrant signaling through the Akt kinase and the ERK mitogen activated protein kinase (MAPK) pathways, in which phosphorylated-Akt (p-Akt) is necessary for survival of the leukemia cells. (Cuni et al. 2004) (Longo et al. 2008) The observation of aberrantly activated Akt and downstream pathways in CLL cells also suggests that the normal regulator of these pathways, PP2A, is unable to perform its normal role.

Non-Hodgkin's lymphoma is a lymphoma characterized by malignant growth of B lymphocytes. Many non-Hodgkin's lymphoma patients have intermediate- or high-grade disease, which are much more aggressive at the time of diagnosis than low-grade disease. The distinction among the grades of non-Hodgkin's lymphoma is important and can have a strong impact on the treatment regimen selected for the patient. Patients with low-grade non-Hodgkin's lymphoma may survive an average of 5-7 years with conventional therapies, whereas patients with intermediate or high grade non-Hodgkins lymphoma have an average survival rate of 2-5 years or 6 months to 2 years, respectively.

There is a need in the art for methods of predicting the level of severity of cancers or linking the progression of cancers with particular markers. In addition, means for making rapid determinations with regard to such markers in clinical diagnostic labs are also needed. The present invention addresses these and other needs.

SUMMARY OF THE INVENTION

In one aspect, the invention relates to a method of predicting or assessing the level of severity of cancer or cancer progression in a patient comprising measuring the level of SET expression in a biological sample from a patient and optionally in a control sample, and comparing the measured level of SET expression in the biological sample to the level of SET expression in the control sample or a standard reference value or range of values, wherein the measured level of SET expression in the biological sample is indicative of the level of severity of cancer or cancer progression in the patient. In one embodiment, the expression level of the alpha and beta isoforms of SET are measured. In another embodiment, an increase in the level of expression of both isoforms relative to the level in a control sample or standard reference value is indicative of a more severe form of cancer or later stage of cancer progression.

In one embodiment, the method provided comprises contacting the biological sample with a SET-specific antibody. In a further embodiment, the level of SET expression is detected by imaging or by flow cytometry. In another embodiment, the SET specific antibody is specific for the alpha isoform of SET. In a still further embodiment, an increase in the level of expression of the alpha isoform relative to the level in a control sample or standard reference value is indicative of a more severe form of cancer or a later stage of cancer progression. In another embodiment, the SET specific antibody is specific for the beta isoform of SET. In a further embodiment, an increase in the level of expression of the beta isoform relative to the level in a control sample or standard reference value is indicative of a more severe form of cancer or a later stage of cancer progression.

In one embodiment, the level of SET expression is measured by performing quantitative PCR using a nucleic acid probe targeting mRNA from either or both SET isoforms. In a further embodiment, the nucleic acid probe targets alpha isoform SET mRNA, and an increase in the level of expression of the alpha isoform relative to the level in a control sample or to a standard reference value is indicative of a more severe form of cancer or later stage of cancer progression. In another embodiment, the nucleic acid probe targets beta isoform SET mRNA, and an increase in the level of expression of the beta isoform relative to the level in a control sample or standard reference value is indicative of a more severe form of cancer or later stage of cancer progression.

In another aspect, the invention relates to a method of predicting or assessing the level of severity of cancer or cancer progression in a patient comprising determining the ratio of SET alpha isoform to SET beta isoform in a biological sample from a patient and comparing the ratio of SET alpha isoform to SET beta isoform in a control sample or a standard reference value or range, wherein the ratio of SET alpha isoform to SET beta isoform in the biological sample is indicative of the level of severity of cancer or cancer progression in the patient. In one embodiment, the ratio of SET alpha isoform to SET beta isoform is determined by contacting the biological sample and optionally a control sample with a SET alpha isoform-specific antibody and a SET beta isoform-specific antibody, measuring the level of SET protein detected by each antibody, and calculating the ratio of SET alpha isoform to SET beta isoform in the biological sample from the patient and optionally in the control sample. In another embodiment, the ratio of SET alpha isoform to SET beta isoform is determined by contacting the biological sample and optionally a control sample with a SET-specific antibody and a SET alpha isoform-specific antibody or a SET-specific antibody and a SET beta isoform-specific antibody, measuring the level of SET protein detected by each antibody, subtracting the level of isoform-specific SET protein from the level of total SET protein measured, and calculating the ratio of SET alpha isoform to SET beta isoform in the biological sample from the patient and optionally in the control sample. Standard reference values or a range of standard values may optionally be used in place of a control. In a further embodiment, the level of SET protein is measured by imaging or by flow cytometry.

In some embodiments, the ratio of SET alpha isoform to SET beta isoform is determined. Quantitative PCR is performed on the biological sample from the patient and optionally a control sample using nucleic acid probes targeting alpha isoform SET mRNA, which binds to both alpha and beta isoform SET. In some embodiments, quantitative PCR is performed on the biological sample from the patient and optionally a control sample using a nucleic acid probe targeting alpha isoform SET mRNA, or beta isoform SET mRNA. The ratio of SET alpha isoform to SET beta isoform in the biological sample and optionally the control sample can be calculated from the results of the quantitative PCR. In further embodiments, the ratio of SET alpha isoform to SET beta isoform is determined by performing quantitative PCR on the biological sample from the patient and the control sample using a nucleic acid probe targeting alpha isoform SET mRNA and a nucleic acid probe targeting both alpha isoform and beta isoform SET mRNA, or a nucleic acid probe targeting beta isoform SET mRNA and a nucleic acid probe targeting SET mRNA, subtracting the level of isoform-specific SET mRNA from the level of total SET mRNA measured, and calculating the ratio of SET alpha isoform to SET beta isoform in the biological sample from the patient and optionally in the control sample. Standard reference values or a range of standard values may optionally be used in place of a control. In a still further embodiment, the nucleic acid probe targeting alpha isoform SET mRNA is according to SEQ ID NO: 7, and the nucleic acid probe targeting beta isoform SET mRNA is according to SEQ ID NO: 10. In a yet further embodiment, the nucleic acid probe targeting alpha isoform SET mRNA is according to SEQ ID NO: 7, the nucleic acid probe targeting beta isoform SET mRNA is according to SEQ ID NO: 10, and the nucleic acid probe targeting both alpha isoform and beta isoform SET mRNA is according to SEQ ID NO: 13.

In one embodiment, an increase in the ratio of SET alpha isoform to SET beta isoform relative to the ratio of SET alpha isoform to SET beta isoform in a control sample or standard reference value is indicative of a more severe form of cancer or later stage of cancer progression.

In some embodiments, the method of predicting or assessing the level of severity of cancer or cancer progression in a patient provided herein further comprises combining the measurement of the ratio of the expression level of the alpha isoform of SET to the beta isoform of SET with other prognostic factors. In further embodiments, the other prognostic factors are selected from the group consisting of IGVH mutation, CD38 expression, and ZAP 70 expression.

In some embodiments, a method of predicting or assessing the level of severity of cancer or cancer progression is provided, and the cancer is selected from the group consisting of chronic lymphocytic leukemia, B-cell non-Hodgkin's lymphoma, breast cancer, prostate cancer, pancreatic cancer, ovarian cancer, and melanoma.

In one embodiment, the invention provides a method of predicting or assessing the level of severity of cancer or cancer progression in a patient comprising measuring the level of SET expression in a biological sample from a patient and optionally in a control sample, optionally comparing the measured level of SET expression in the biological sample to the level of SET expression in the control sample, wherein the measured level of SET expression in the biological sample is indicative of the level of severity of cancer or cancer progression in the patient. In one embodiment, the biological sample is a tumor biopsy from a solid tumor. In a further embodiment, the biological sample is peripheral blood mononuclear cells. In another further embodiment, the biological sample is CD19+/CD5+ B lymphocytes.

In one aspect, the invention relates to a kit comprising at least one reagent for measuring SET expression in a biological sample and instructions for measuring SET expression for assessing the level of severity of cancer or cancer progression in a patient. In one embodiment, at least one reagent in the kit is selected from the group consisting of an anti-SET alpha antibody, an anti-SET beta antibody, a nucleic acid probe targeting SET alpha mRNA, a nucleic acid probe targeting SET beta mRNA, a primer set for amplifying SET alpha mRNA, a primer set for amplifying SET beta mRNA, and combinations thereof.

In another aspect, the invention relates to a method for predicting or evaluating the efficacy of a SET therapeutic for treating cancer in a patient comprising administering a SET therapeutic to the patient, measuring the expression level of SET protein in a biological sample from the patient, and comparing the measured level to the expression level of SET protein in a control sample or a standard value or range, wherein the measured expression level of SET protein is indicative of the therapeutic efficacy of a SET therapeutic. In one embodiment, the expression level of the alpha isoform of SET is measured, and an increase in the level of expression of the alpha isoform relative to the level in a control sample or a standard value or range is indicative that a SET therapeutic would be efficacious in treating cancer in the patient. In another embodiment, the expression level of the beta isoform of SET is measured, and an increase in the level of expression of the beta isoform relative to the level in a control sample or a standard value or range is indicative that a SET therapeutic would be efficacious in treating cancer in the patient. In still another embodiment, the expression level of the alpha and beta isoforms of SET are measured, and an increase in the level of expression of both isoforms relative to the level in a control sample or a standard value or range is indicative that a SET therapeutic would be efficacious in treating cancer in the patient. In a separate embodiment, the expression level of the alpha isoform of SET is measured relative to the expression level of the beta isoform of SET, and an increase in the ratio of the expression level of the alpha isoform to the expression level of the beta isoform as compared to the ratio in a control sample or a standard value or range is indicative that a SET therapeutic would be efficacious in treating cancer in the patient.

In one embodiment, a method for predicting or evaluating the efficacy of a SET therapeutic for treating cancer in a patient comprising administering a SET therapeutic to the patient, measuring the expression level of SET protein in a biological sample from the patient, and comparing the measured level to the expression level of SET protein in a control sample or a standard value or range, wherein the measured expression level of SET protein is indicative of the therapeutic efficacy of a SET therapeutic is provided, and the SET therapeutic is an ApoE peptide or peptide dimer. ApoE peptides and peptide dimers have previously been described in PCT publication No. WO/2011/085110, incorporated by reference herein in its entirety. In a further embodiment, a measured SET expression level of at least 2-fold relative to the control sample is predictive of therapeutic efficacy of an ApoE peptide or peptide dimer for treating cancer in the patient. In another embodiment, the SET therapeutic is a small interfering RNA or a short hairpin RNA targeting SET mRNA. In another embodiment, the method comprises administering at least one SET therapeutic to the patient. In still another embodiment, the biological sample is a tumor biopsy from a solid tumor. In a further embodiment, the solid tumor is breast cancer, pancreatic cancer, prostate cancer, ovarian cancer, melanoma, or lymphoma.

In one embodiment, the invention relates to a method for predicting or evaluating the efficacy of a SET therapeutic for treating cancer in a patient comprising administering a SET therapeutic to the patient, measuring the expression level of SET protein in a biological sample from the patient, and comparing the measured level to the expression level of SET protein in a control sample or a standard value or range, wherein the measured expression level of SET protein is indicative of the therapeutic efficacy of a SET therapeutic, and the biological sample is peripheral blood mononuclear cells. In a further embodiment, the biological sample is CD19+/CD5+ B lymphocytes.

In another embodiment, the invention relates to a method of treating cancer in a patient comprising measuring the level of SET expression in a biological sample from the patient, and determining a method of treatment based on the level of SET expression relative to the level in a control sample or a standard value. Methods of cancer treatment have been previously described in PCT publication No. WO2010/002982, incorporated by reference herein in its entirety. In another embodiment, the invention relates to a method of treating cancer in a patient comprising measuring the level of alpha isoform SET or beta isoform SET expression in a biological sample from the patient, and determining a method of treatment based on the level of alpha isoform SET or beta isoform SET expression relative to the level in a control sample or a standard value.

In another embodiment, the invention provides a method of treating cancer in a patient comprising determining the ratio of SET alpha isoform to SET beta isoform in a biological sample from the patient, and determining a method of treatment based on the ratio of SET alpha isoform to SET beta isoform relative to the ratio in a control sample or a standard value. In a further embodiment, the method further comprises combining the measurement of the ratio of the level of SET alpha isoform to SET beta isoform with other prognostic factors. In yet a further embodiment, the other prognostic factors are selected from the group consisting of IGVH mutation, CD38 expression, and ZAP 70 expression.

In one embodiment, the invention relates to a kit comprising at least one reagent for measuring SET protein expression in a biological sample and instructions for measuring SET protein expression for predicting or evaluating the efficacy of a SET therapeutic for treating cancer in a patient. In a further embodiment, the at least one reagent is selected from the group consisting of an anti-SET alpha antibody, an anti-SET beta antibody, a nucleic acid probe targeting SET alpha mRNA, a nucleic acid probe targeting SET beta mRNA, a primer set for amplifying SET alpha mRNA, a primer set for amplifying SET beta mRNA, and combinations thereof.

Figure 3:
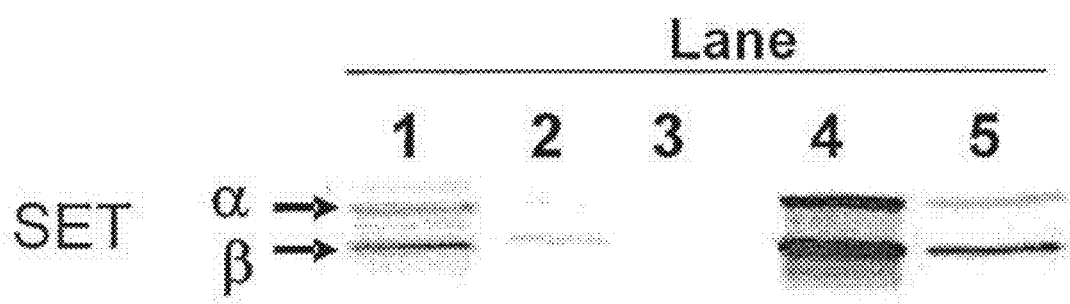
FIG. 3: COG peptides binds to both SET isoforms from primary human CLL cells. A lysate CLL cells from a patient was prepared and mixed with or without biotin-COG112 or biotin-COG133. Complexes bound to Neutravidin-Agarose (NA) beads were then detected by Western blotting. Lane 1 contains 20 μg of cell lysate as a loading control. Lanes 2-5 contain extract from 300 μg of lysate incubated with either buffer (lane 2), 10 μM biotin (lane 3), 10 μM Biotin-labeled COG133 (lane 4) or 10 μm Biotin-labeled COG112 (lane 5). Lysates were incubated with biotin reagents for 1 hr before addition of NA beads and then incubated for an additional hour. After rigorous washing, the beads were boiled in SDS PAGE buffer, separated by PAGE and blotted to nitrocellulose. SET appears as bands at ~39 (β) and 41 kDa (α) that bound to the biotin-labeled COG112/133 (lanes 4 &5), but not in buffer alone (lane 2) or biotin only lanes (lane 3).
Figure 4:
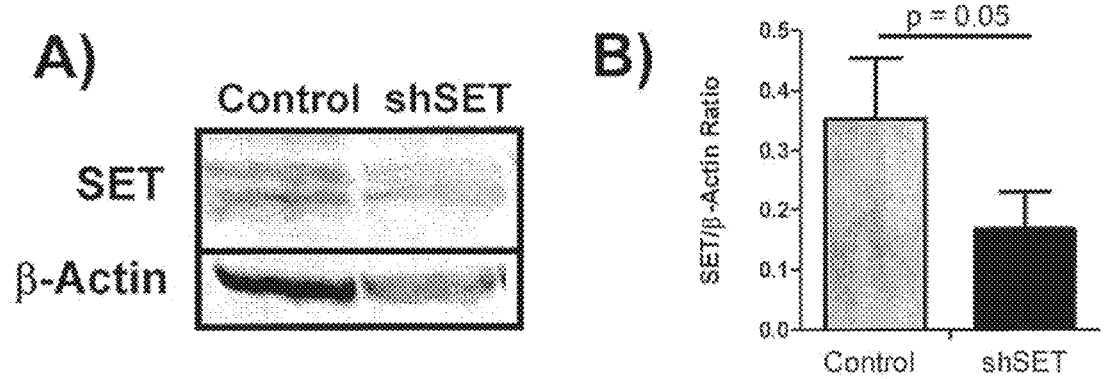

FIG. 4: Silencing of SET inhibits SET protein expression in 32D:BCR/Abl cells. The cells used for PP2A phosphatase activity assays in FIG. 3B were assessed by immunoblot to quantify the level of knockdown of SET. (A) Western blots show that SET protein levels were reduced in the cells, and (B) quantitation of the SET levels show an approximate 50% reduction (n=3) relative to β-Actin loading controls (*=p<0.05 by T-test).

Figure 5:
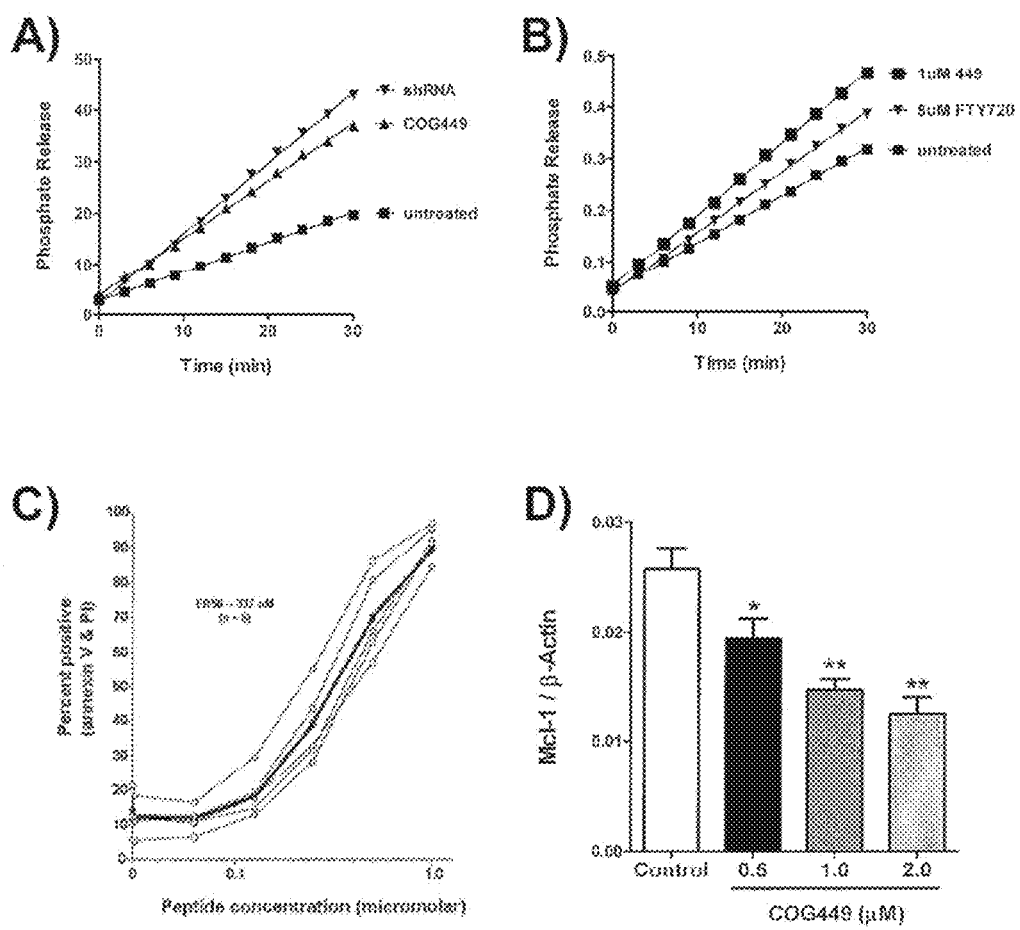

FIG. 5: SET antagonism activates PP2A, induces apoptosis, and reduces Mcl-1 levels. (A) SET was knocked down by shRNA to SET following lentiviral transduction in 32D:BCR/Abl cell cultures or treatment with 1 μM COG449 followed by lysis with NP40 lysis buffer. PP2A was immunoprecipitation and assayed with the PP2A immunoprecipitation assay kit (Upstate), with the exception of using DiFMUP as a fluorescent substrate. The line for each sample represents the phosphate release from a given sample following subtraction of the OA inhibited control reactions (p<0.05) (B) 32D:BCR/Abl cells were treated with the indicated compounds for 30 minutes followed by lysis with NP40 lysis buffer. PP2A was immunoprecipitated and assayed as in panel A (p<0.01). (C) CLL cells were treated with COG449 followed by annexin-V and propidium iodide staining to assess apoptosis and death. (D) Freshly-isolated human CLL cells were incubated with the indicated concentrations of COG449 for 24 hrs. Cells were lysed, protein lysates subjected to PAGE, and immunoblotted to quantify the Mcl-1 and β-Actin ratio (*indicates p<0.01, **indicates p<0.001 relative to control).

Figure 6:
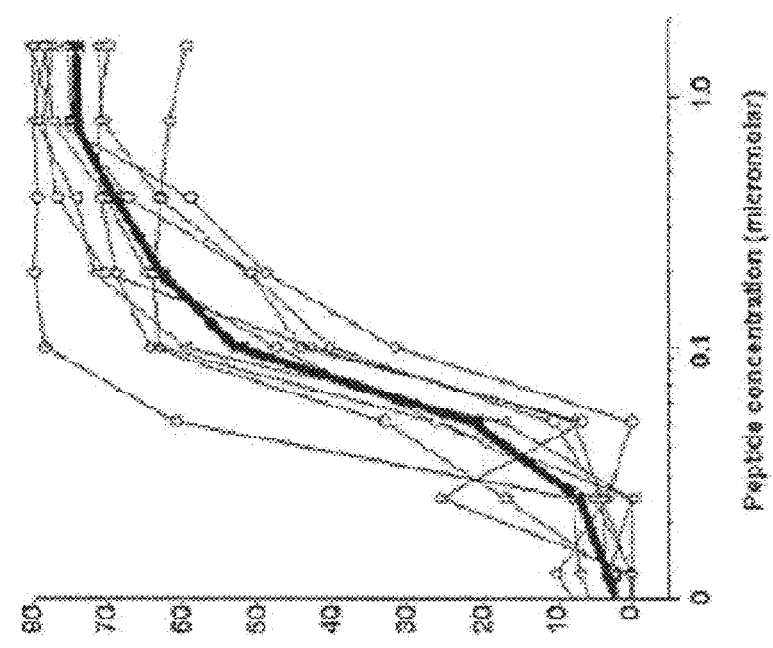
Figure 6:
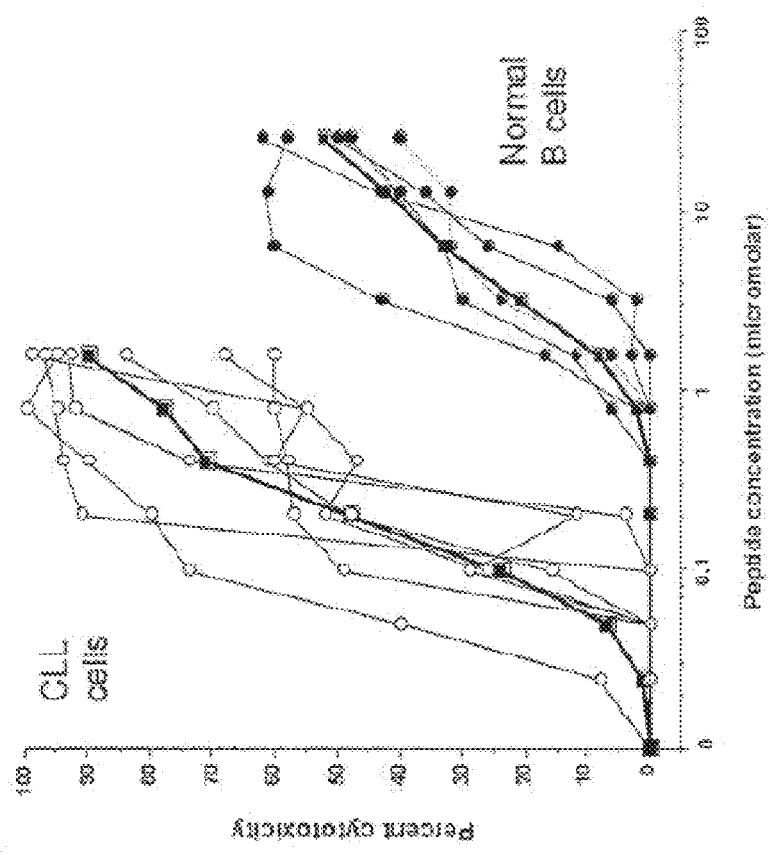
Figure 6:
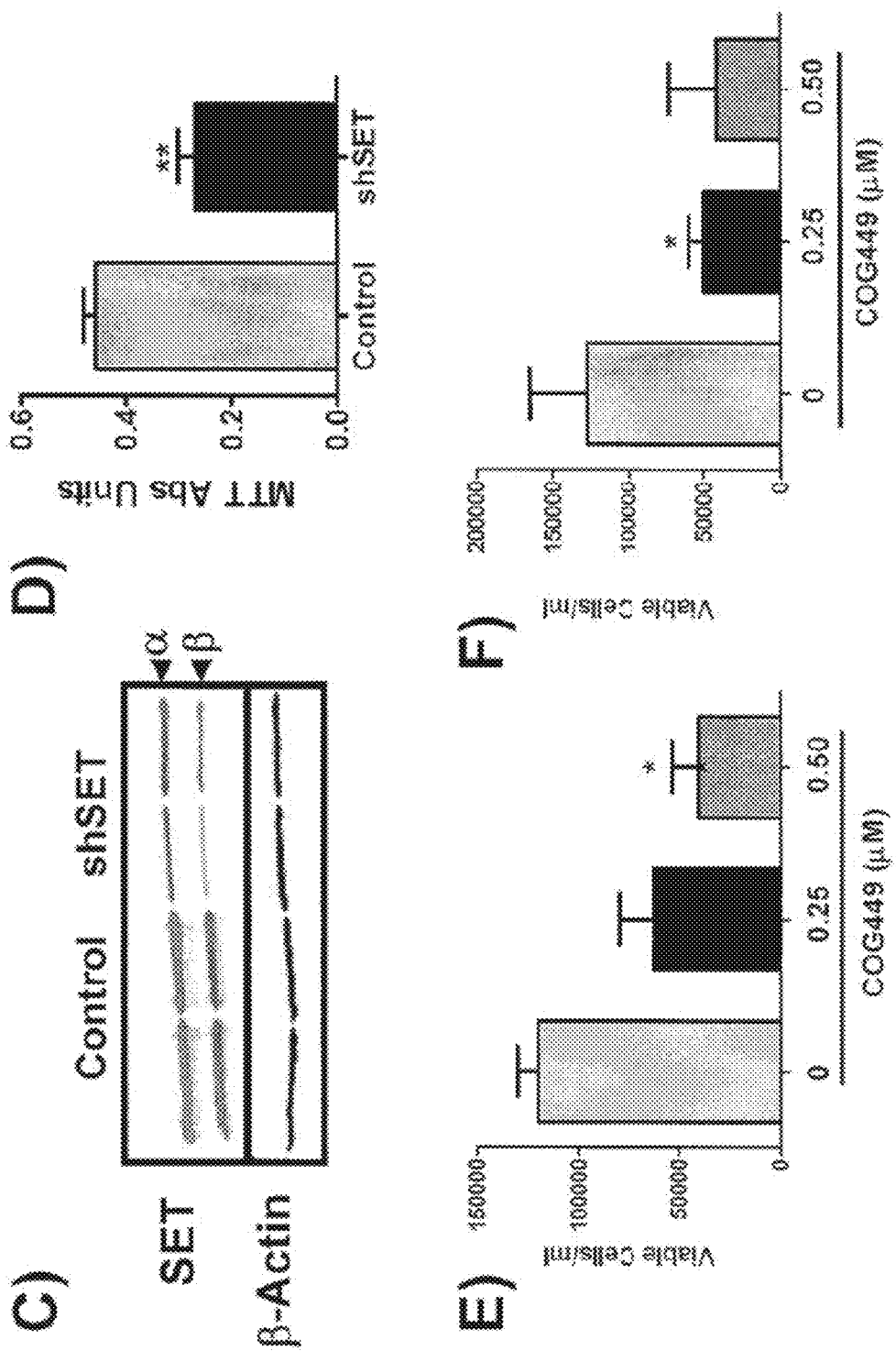

FIG. 6: SET antagonism is cytotoxic to CLL cells and inhibits NHL cell growth in vitro. (A) Dose response curves for COG445 treatment of CLL cells from 7 patients or normal B-cells from 5 volunteers. (B) Dose response curves for COG449 treatment on CLL cells from 7 patients. (C) Raji NHL cells were transduced with SET shRNA or control lentivirus and knockdown was assessed by Western blotting from two samples of each. (D) Growth of Raji cells from Panel C was assessed 72 hr after knockdown using a tetrazolium assay, and demonstrated that SET antagonism inhibited growth (**=p<0.01). (E) Growth inhibition of Raji cells treated with the indicated levels of COG449 for 72 hr. (F) Growth inhibition of Ramos cells treated with the indicated levels of COG449 for 72 hr.

Figure 7:
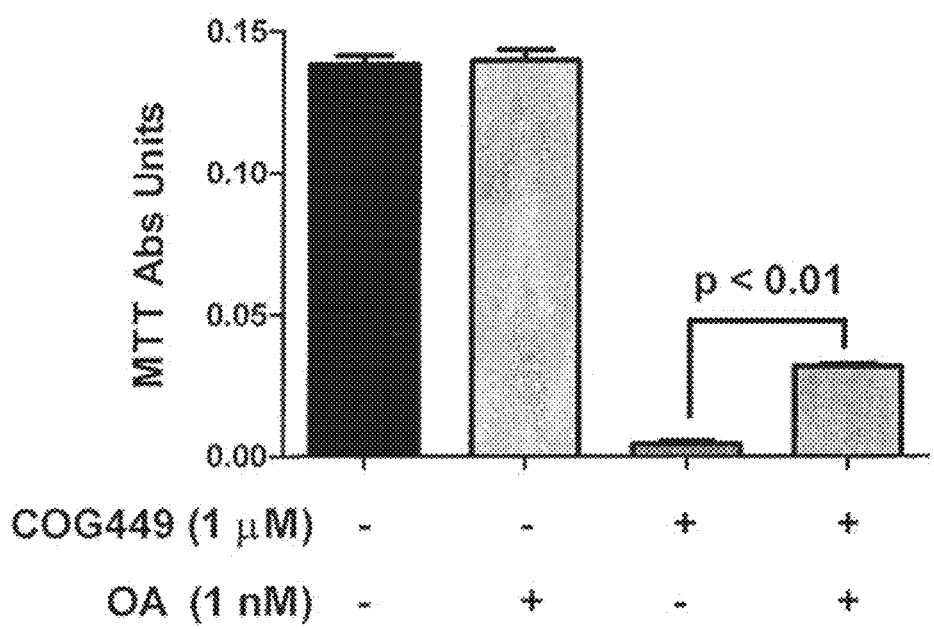

FIG. 7: Cytotoxicity of COG449 can be modulated by a PP2A inhibitor in Ramos cells. Ramos cells were pretreated for 5 minutes with or without 1 nM OA before treatment with 1 μM COG449. After 24 hours, cytotoxicity was assessed using the MIT assay reagent to detect viable cells. Treatment with OA alone was not significantly cytotoxic while COG449 robustly inhibited growth. When COG449 treatment was preceded by OA treatment the cytotoxicity was significantly reduced indicating that PP2A plays a role in the cytotoxicity of COG449.

Figure 8:
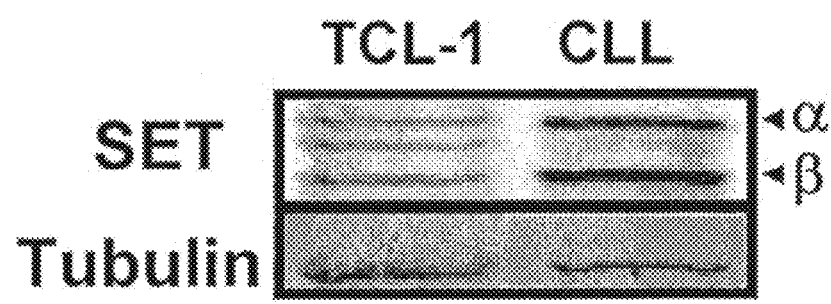

FIG. 8: SET expression in TCL-1 mouse CD19+ cells. CLL-like CD5+ cells were purified from the spleen of a transgenic TCL-1 mouse with splenomegaly and a lysate was prepared from the purified mouse (left lane) and primary human CD5+/CD19+ CLL cells (right lane). Western blotting was performed to determine SET expression level in the mouse and human cells relative to a tubulin loading control.

Figure 9:
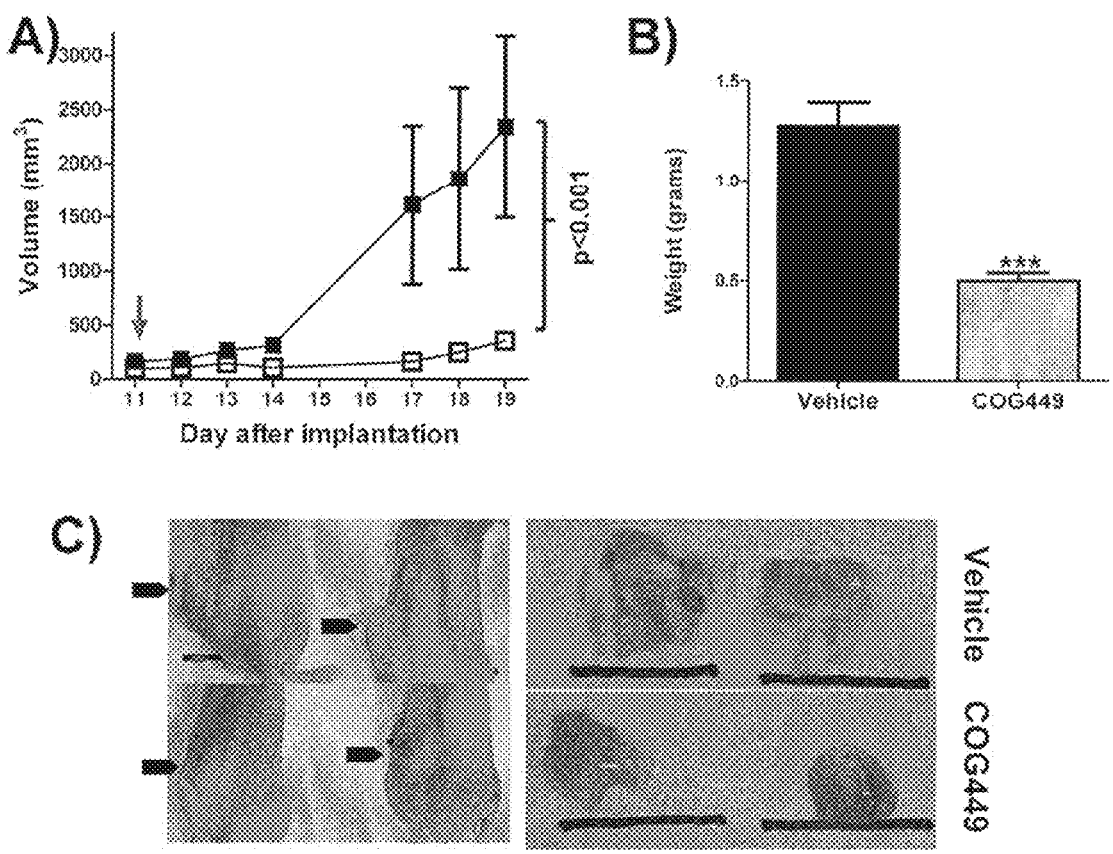

FIG. 9: SET antagonism inhibits NHL cell growth in vivo. (A) Tumor volumes of Ramos cell tumor xenografts in SCID mice following in vivo treatment with 5 mg/kg COG449 (open squares) or lactated Ringer's solution control (filled squares) by subcutaneous injection. The injections were initiated on day 11, once tumors reached palpable sizes of 50-100 mm$^3$. (B) Final tumor mass for treated and untreated Ramos tumors harvested on day 19 after implantation. ***=p<0.001 by t-test. (C) The photographs display representative mice and their tumors.

Figure 10:
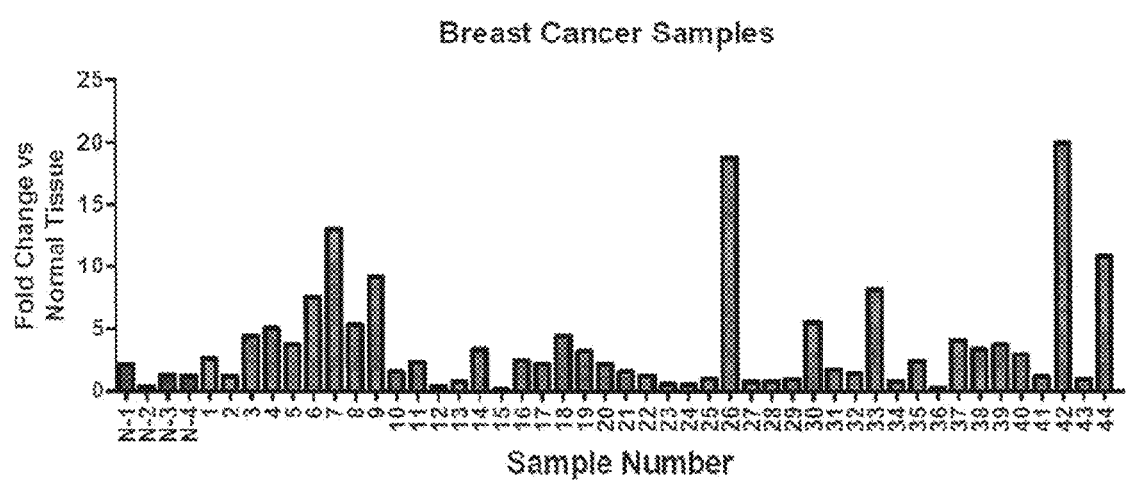

FIG. 10 SET expression by qPCR in tumor samples from breast cancer patients (sample numbers 1-44) compared to normal tissue samples (sample numbers N1-N4).

Figure 11:
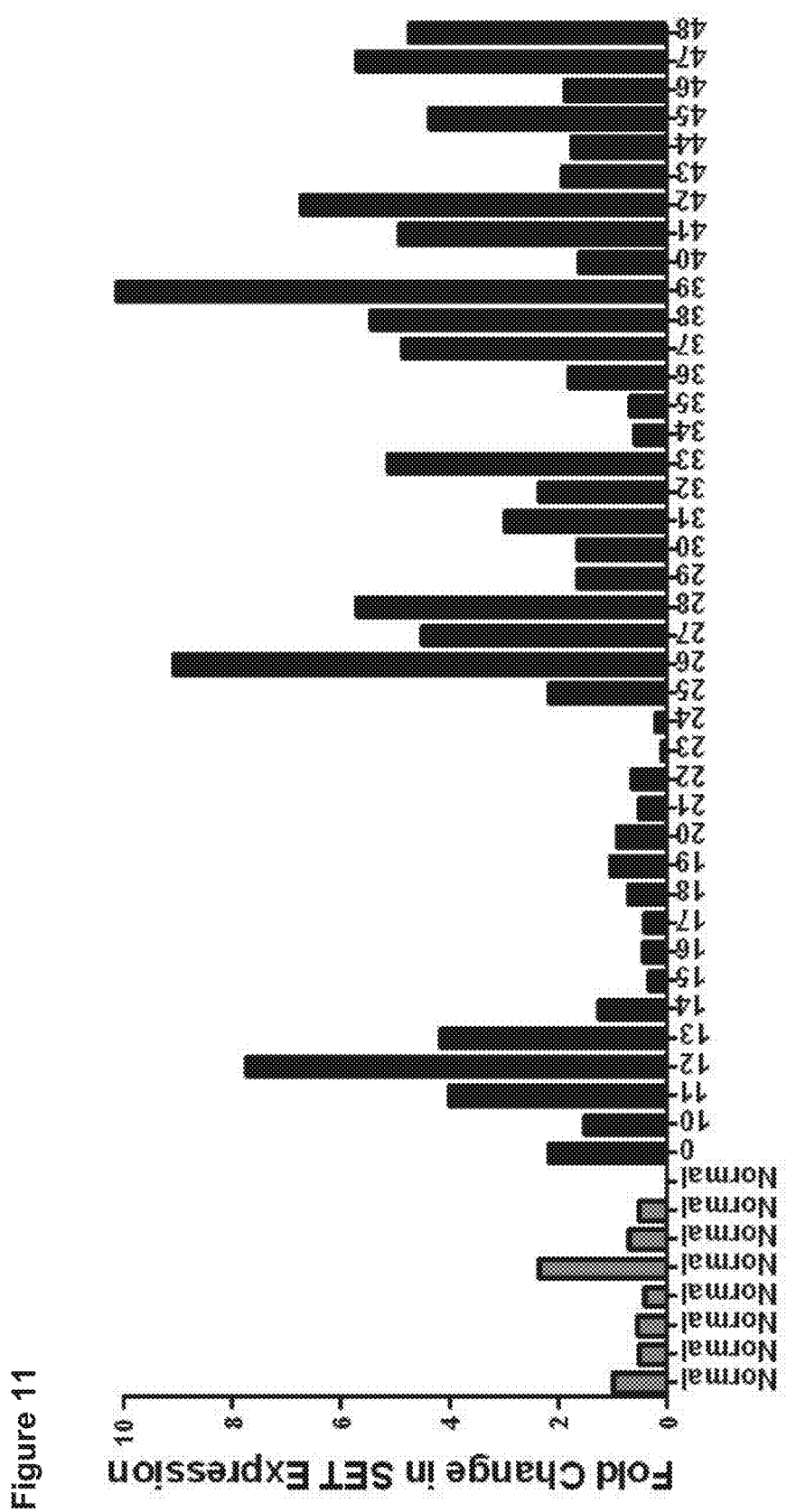
Figure 11:
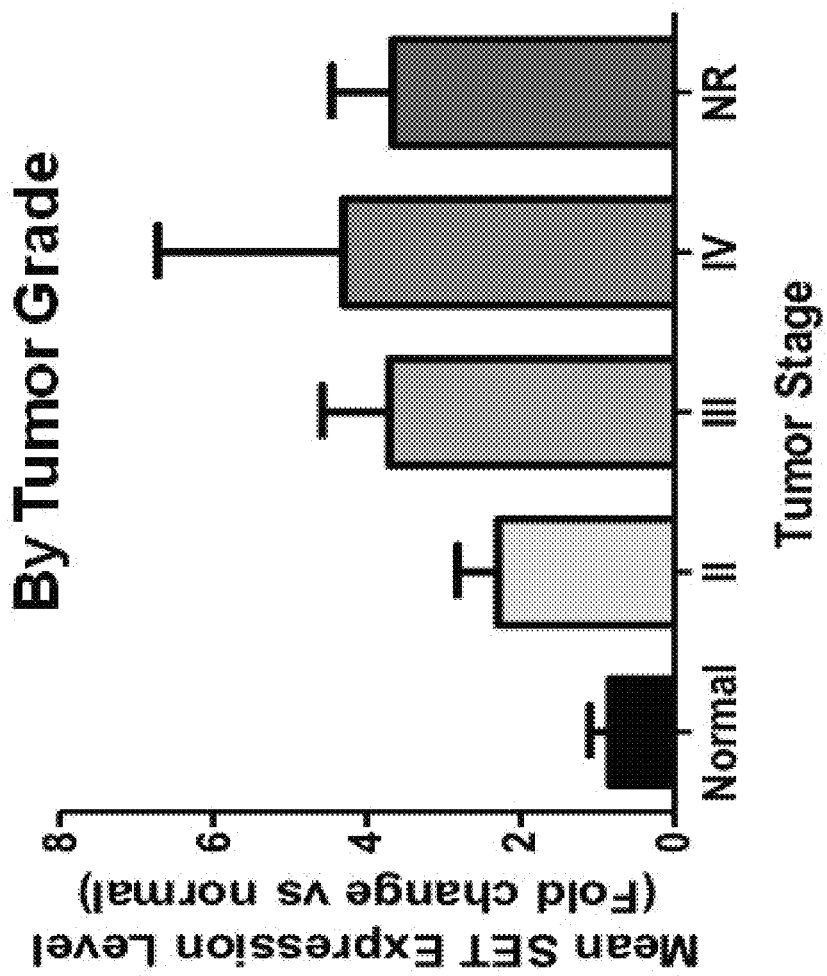

FIG. 11. SET expression by qPCR in tumor samples from prostate cancer patients compared to normal tissue samples. All samples are shown in the upper panel. The lower panel depicts SET expression by the grade of tumor. NR=not reported.

Figure 12:
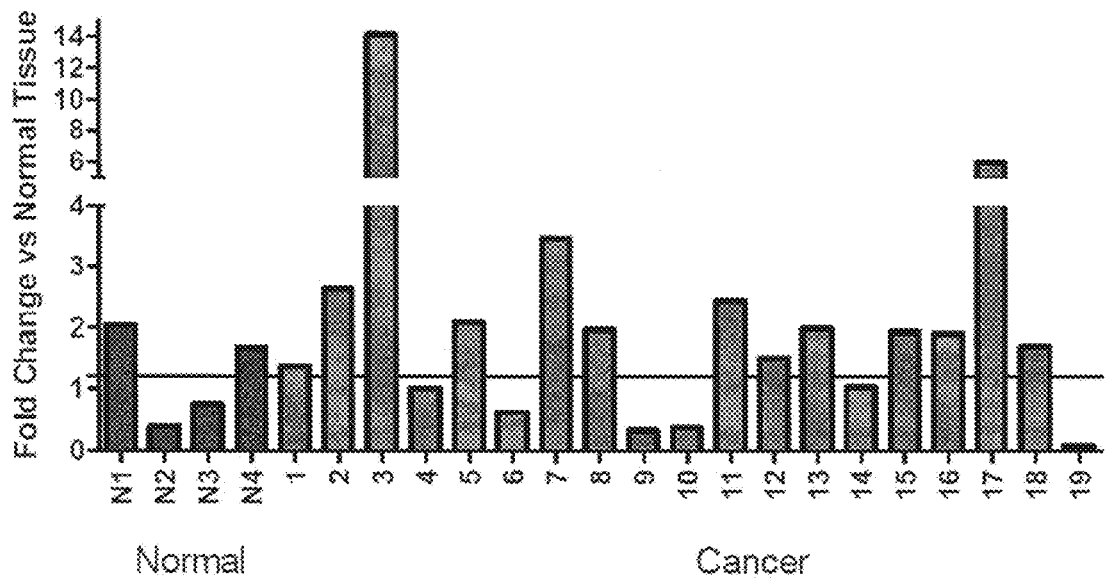

FIG. 12. SET expression by qPCR in tumor samples from pancreatic cancer patients (sample numbers 1-19) compared to normal tissue samples (sample numbers N1-N4).

Figure 13:
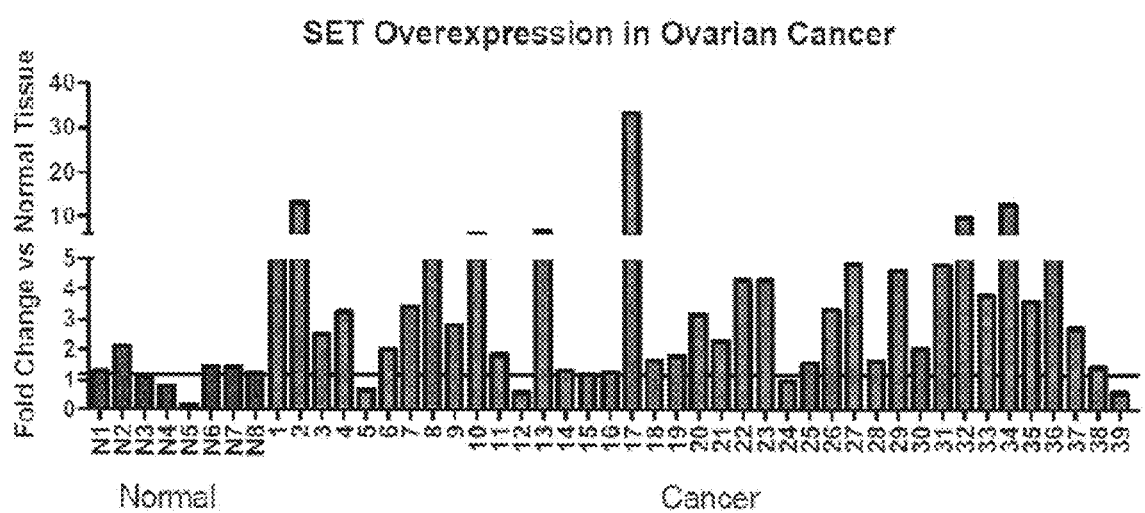

FIG. 13. SET expression by qPCR in tumor samples from ovarian cancer patients (sample numbers 1-39) compared to normal tissue samples (sample numbers N1-N8).

Figure 14:
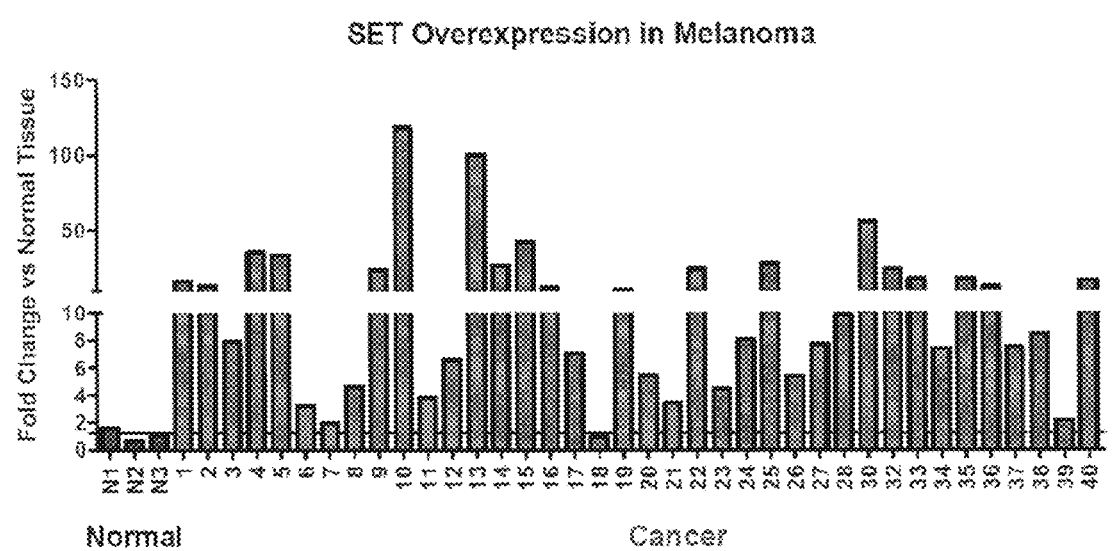

FIG. 14. SET expression by qPCR in tumor samples from melanoma patients (sample numbers 1-40) compared to normal tissue samples (sample numbers N1-N3).

Figure 15:
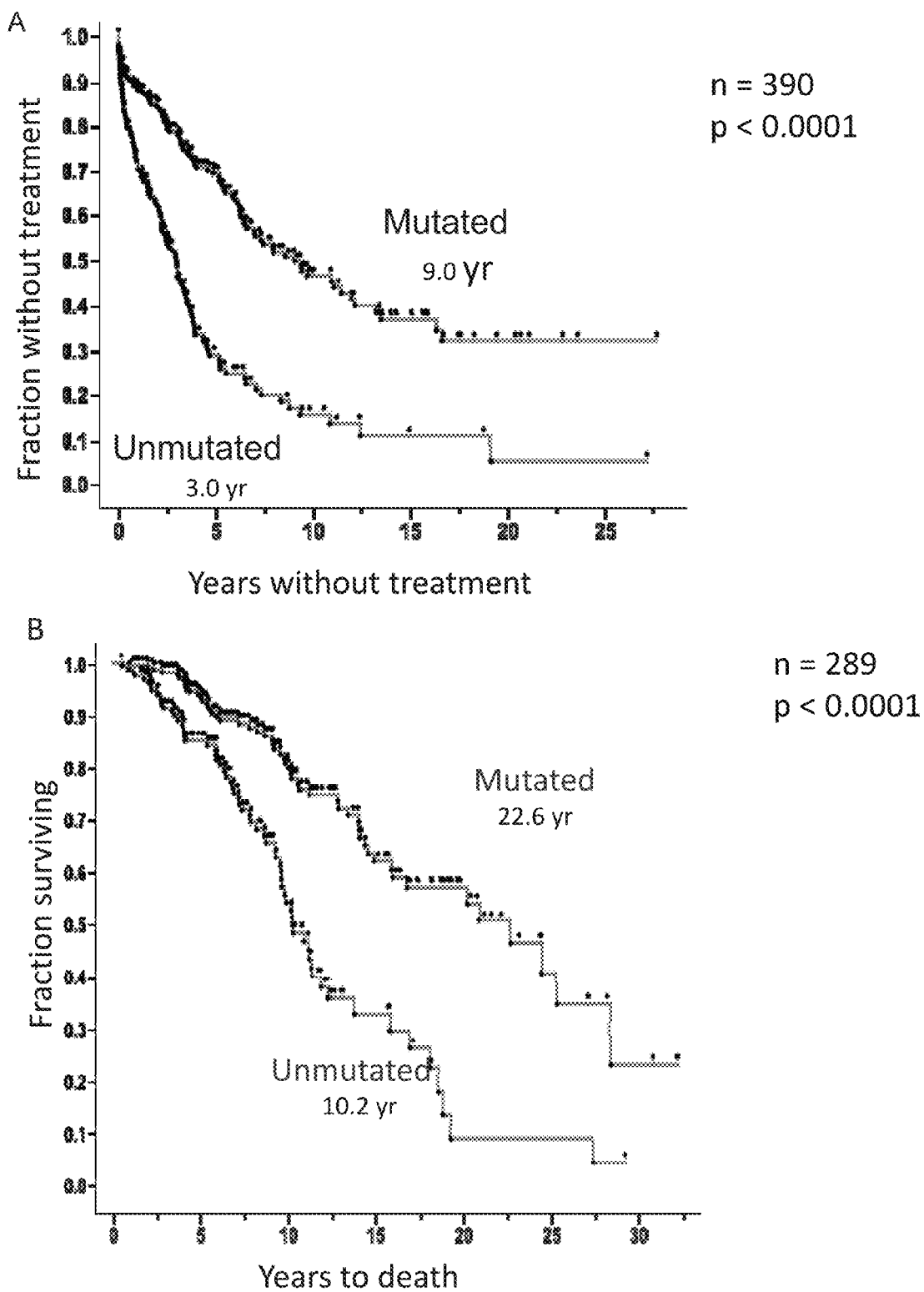

FIG. 15. Time To Treatment (TTT; FIG. 15A) and overall survival (FIG. 15B) is shorter in patients carrying unmutated IGVH (red line) compared to those with mutated IGVH (blue line).

Figure 16:
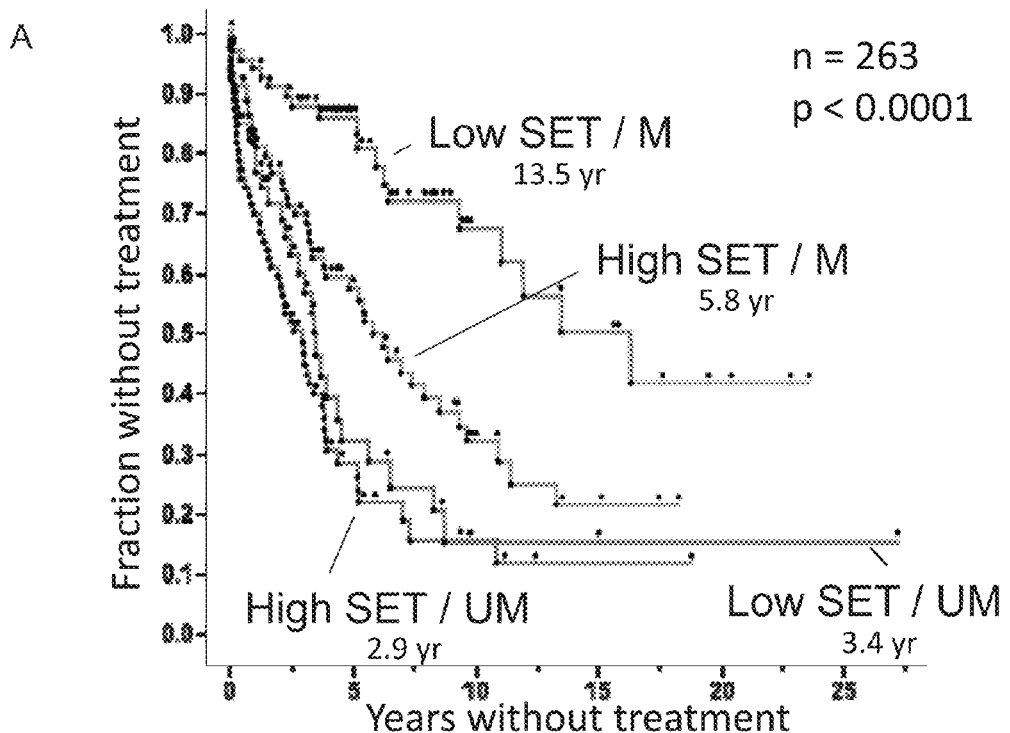
Figure 16:
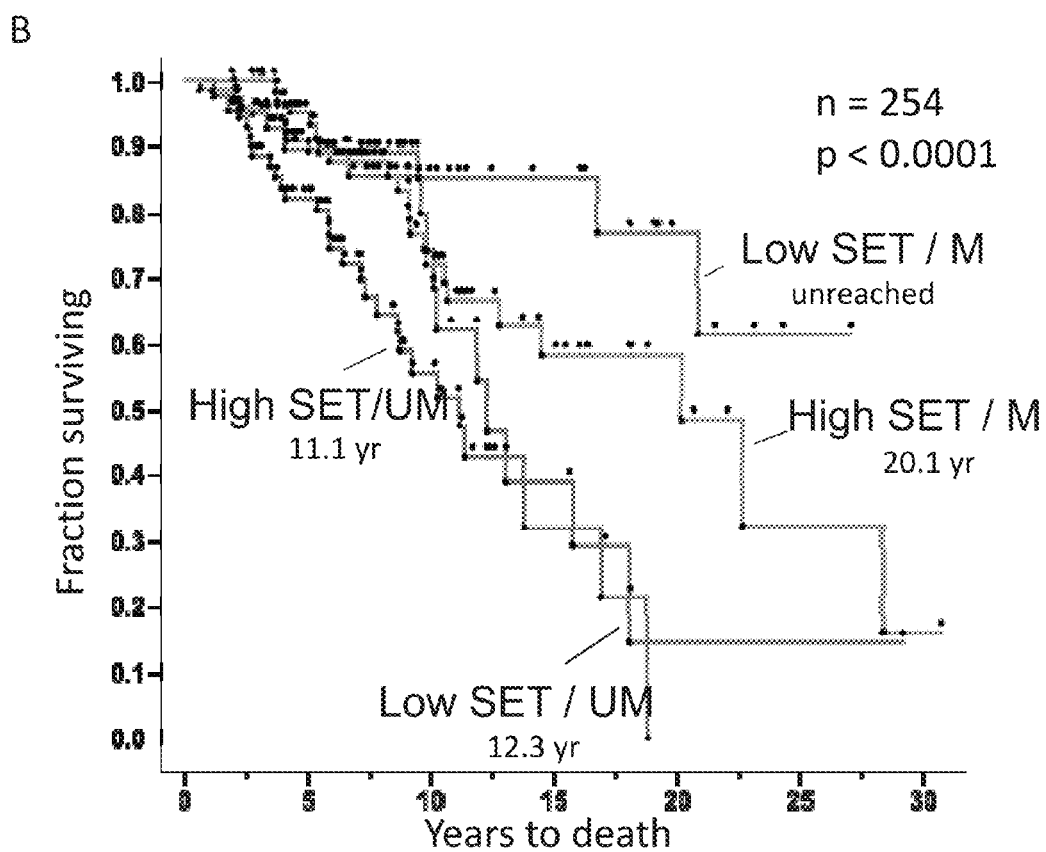

FIG. 16. Combining mutation status and SET α/β ratio increases prognostic power. FIG. 16A shows that TTT is shorter in patients carrying mutated IGVH and low SET α/β ratios (median TTT=13.5) compared to patients with mutated IGVH and high SET α/β ratios (median TTT=5.8 years). FIG. 16B shows that overall survival time is longer in patients carrying mutated IGVH and low SET α/β ratios (median time to death not yet reached) compared to patients with mutated IGVH and high SET α/β ratios (median time to death 20.1 years).

Figure 17:
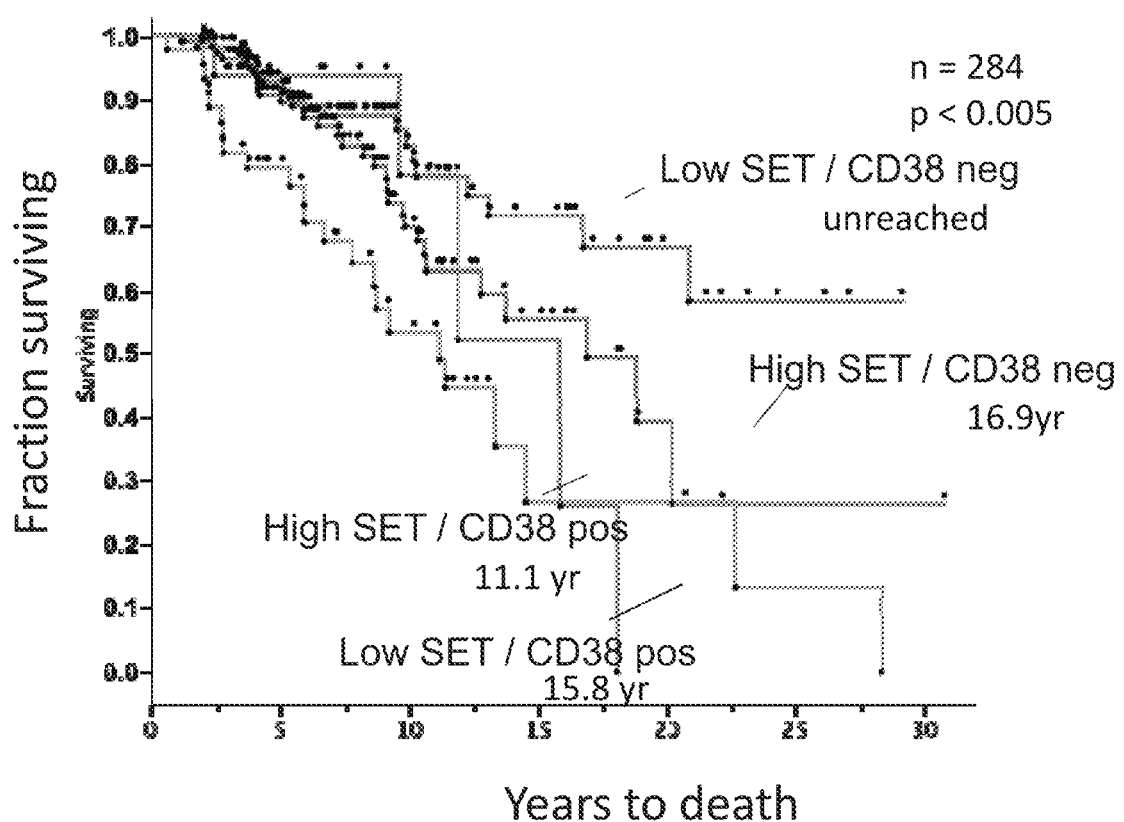

FIG. 17. Overall survival time is longer in patients with low CD38 expression and low SET α/β ratios (median time to death not yet reached) compared to patients with low CD38 expression and high SET α/β ratios (median time to death 16.9 years).

Figure 18:
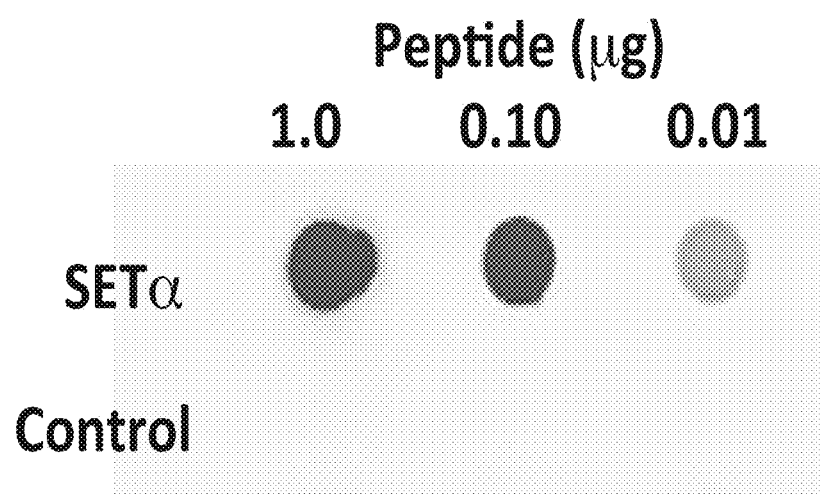

FIG. 18. Sera from a rabbit immunized with a SETα specific peptide was used in a dot blot against a dilution series of the SETα peptide (top row) or a control peptide from the internal region of SET (bottom row) showing positive antibody production.

Figure 19:
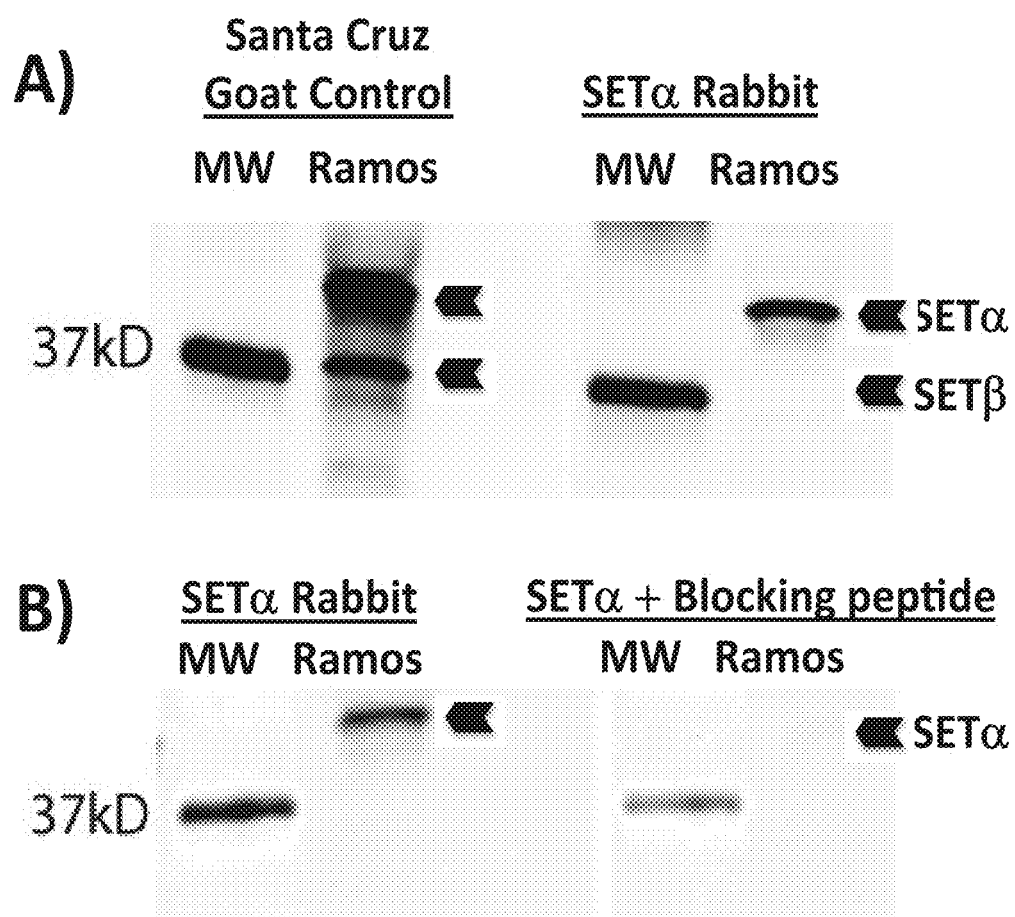

FIG. 19. Selective SETα antibody confirmation on Western blots. A) Sera from either a commercial total-SET (left) or a rabbit immunized with a SETα specific peptide (right) was used in Western blot against a Ramos cell line extract that shows both the SETα and SETβ isoforms. The SETα sera does not recognize the lower MW SETβ band. B) Sera from the SETα rabbit was used in Western blot against a Ramos cell line extract either alone or after preincubation with 10 μg of the blocking peptide, which shows that the SETα antibody is blocked by the antigen used to generate the antibody response.

Figure 20:
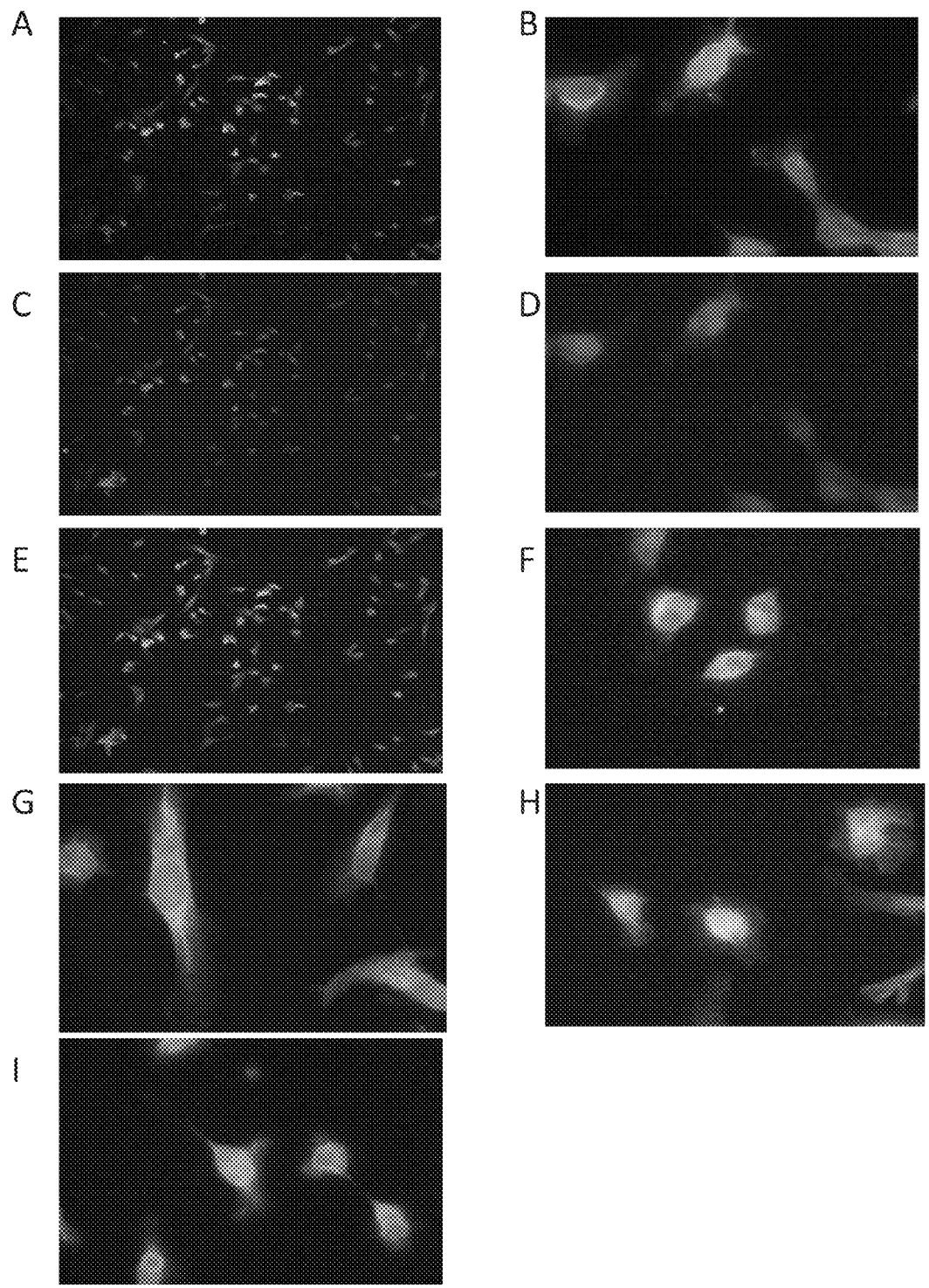

FIG. 20. MDA-MB-231 cells stain with total SET antibody (A, 20×; B, 100×), with alpha isoform-specific SET (COG16; C, 20×; D, 100×), or with both antibodies (E, 20×; F-I, 100×).

Figure 21:
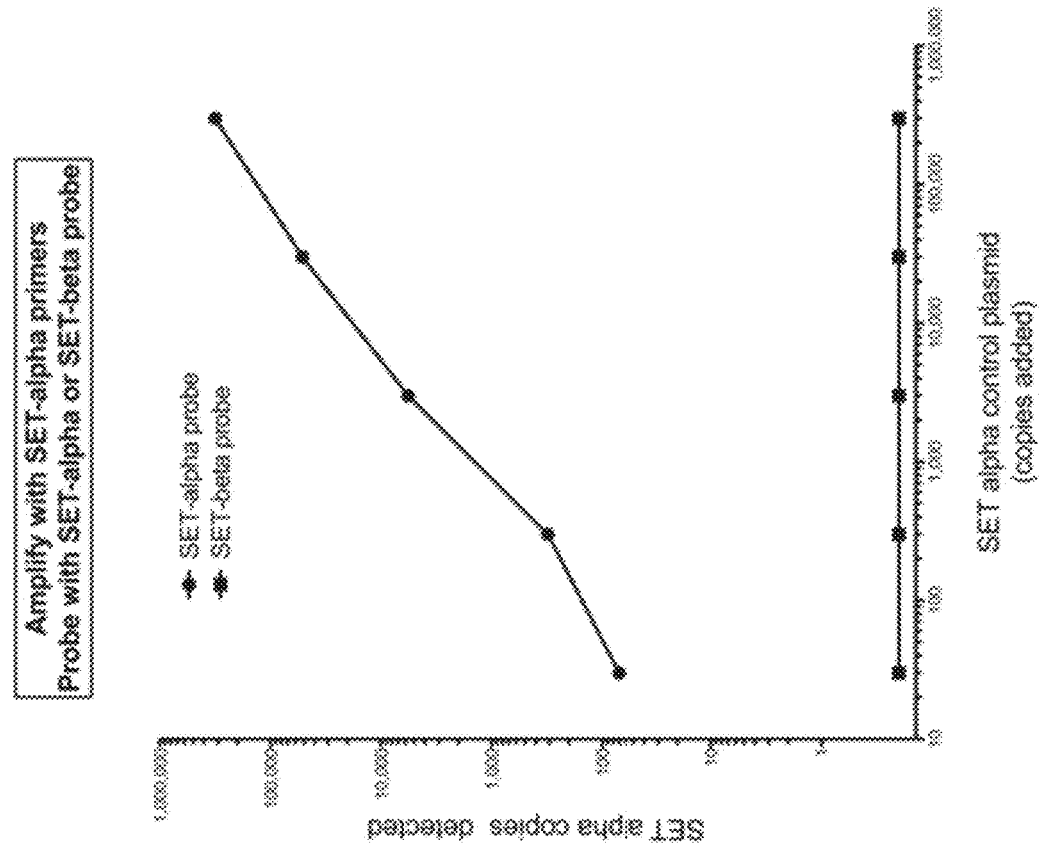
Figure 21:
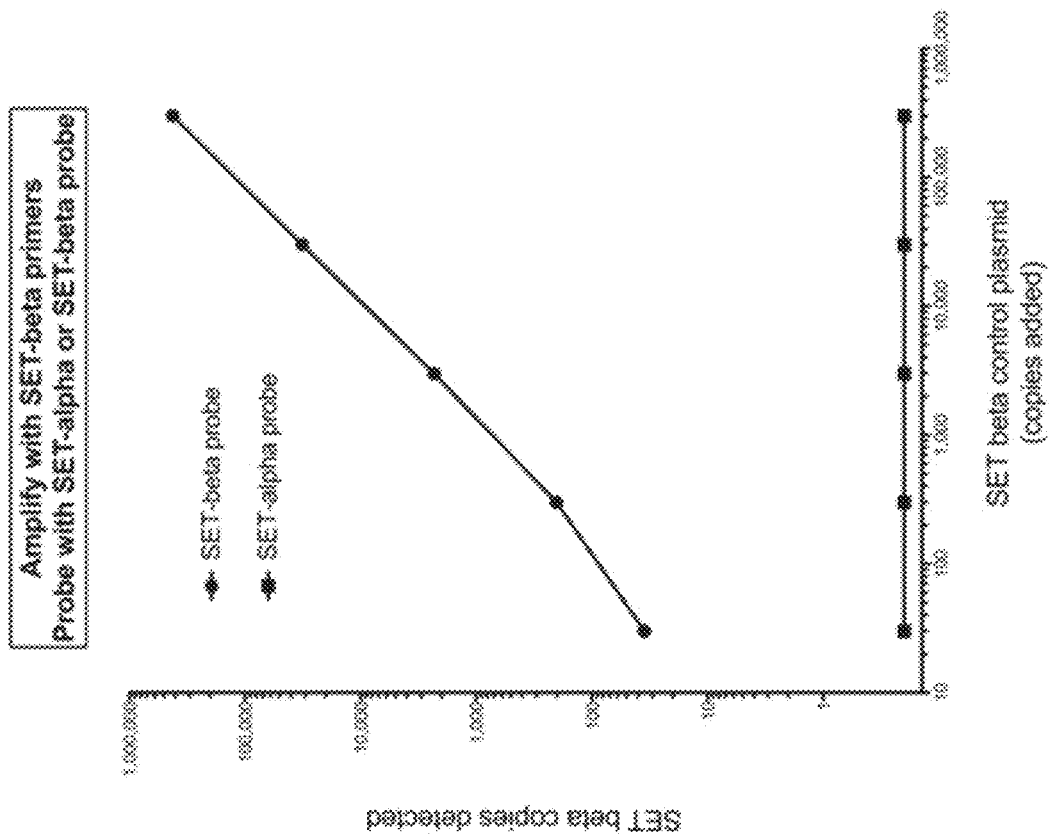

FIG. 21. The isoform-specific primers specifically amplified the SET isoform of interest, as measured by qPCR.

Figure 22:
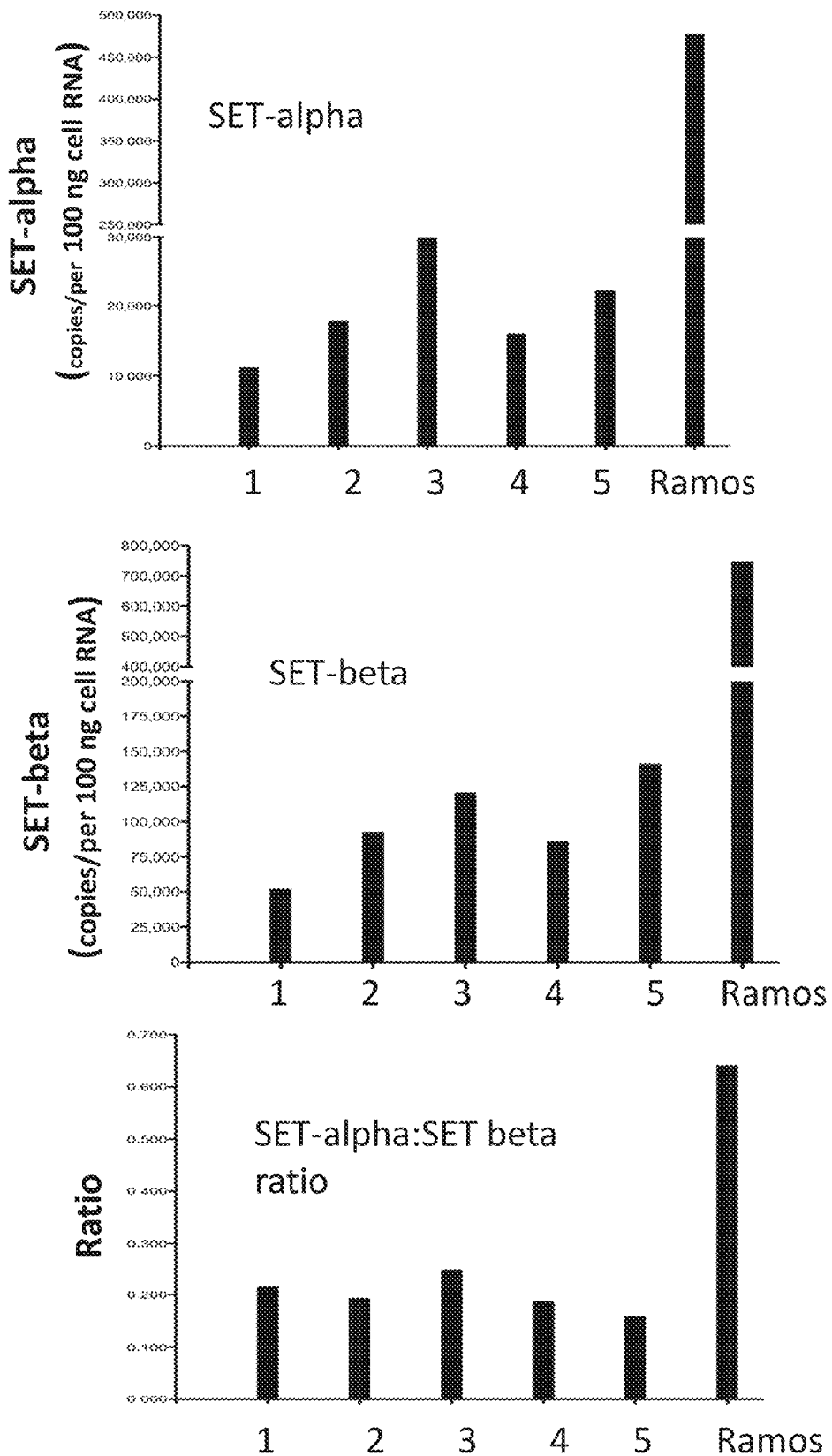

FIG. 22. The isoform-specific primers specifically detected SET alpha isoform and SET beta isoform mRNA in biological samples from CLL patients. Using the results of the quantitative PCR, the ratio of SET alpha isoform to SET beta isoform was determined in the biological samples.

DETAILED DESCRIPTION OF THE INVENTION

The present invention is based on the discovery that the levels of SET present in a biological sample and the ratio of SET protein isoforms SET α and SET β in the biological sample can be measured and are prognostic indicators of cancer severity or progression. Accordingly, the present invention provides methods of combining steps to measure levels of total SET, SET α, and/or SET β and use the measurements to predict the level of severity of cancer or cancer progression in the patient. The present invention also provides methods of combining steps to measure the ratio of the SET α to SET β isoforms, and use the measurements to predict the level of severity of cancer or cancer progression in the patient. The disclosed methods can be performed, using the disclosed techniques, to measure total SET, SET α, SET β, or a combination thereof.

The SET protein is a potent physiological inhibitor of protein phosphatase 2A (PP2A) (Li et al. 1996) that was isolated from a chromosomal rearrangement at 9q34 in a patient with acute undifferentiated leukemia (Adachi et al. 1994). The two isoforms of SET arise from differential splicing, and their expression is driven by distinct promoters for the α- and β-isoforms. The isoforms differ only in the N-terminal portion of the protein in which the α-isoform has a 37 amino acid N-terminal region that arises from Exon 1 of the SET gene while the β-isoform has a 24 amino acid N-terminal region that arises from Exon 2 of the SET gene. The remaining 253 amino acids are identical in each isoform and arise from Exons 3-9. (Asaka et al. 2008) The mechanisms that regulate expression of each of these isoforms has not been fully elucidated.

As used herein, the use of the word "a" or "an" may mean "one," but it is also consistent with the meaning of "one or more," "at least one," and "one or more than one."

The term "subject" is used interchangeably herein with the term "patient" and means any mammalian subject. In some embodiments, the subject is a human subject.

As used herein, the term "biological sample" refers to a sample obtained from a subject, including sample of biological tissue or fluid origin obtained in vivo or in vitro. Biological samples can be, without limitation, body fluid (e.g., blood, blood plasma, serum, or urine), organs, tissues, fractions and cells isolated from mammals including, humans. Biological samples also may include sections of the biological sample including tissues (e.g., sectional portions of an organ or tissue). Biological samples may also include extracts from a biological sample, for example, an antigen from a biological fluid (e.g., blood or urine). Biological samples may be dispersed in solution or may be immobilized on a solid support, such as in blots, assays, arrays, glass slides, microtiter, or ELISA plates.

As used herein, the symbol "α" is used interchangeably with the term "alpha." The symbol "β" is used interchangeably herein with the term "beta."

In one embodiment, a method of predicting or assessing the level of severity of dancer or cancer progression in a patient is provided. In some embodiments, the cancer is selected from the group consisting of chronic lymphocytic leukemia, B-cell non-Hodgkin's lymphoma, breast cancer, prostate cancer, pancreatic cancer, ovarian cancer, melanoma, colorectal cancer, head and neck cancer, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, neuroblastoma, retinoblastoma, leukemias, lymphomas, multiple myeloma, Waldenstrom's macroglobulinemia, myelodysplastic disease, heavy chain disease, neuroendocrine tumors, and Schwanoma.

In some embodiments, the level of SET expression is measured by contacting the biological sample with a SET-specific antibody. A SET-specific antibody may be for example a polyclonal antibody, a monoclonal antibody, a chimeric antibody, a human antibody, an affinity maturated antibody or an antibody fragment. While monoclonal antibodies are highly specific to a marker/antigen, a polyclonal antibody can preferably be used as a capture antibody to immobilize as much of the marker/antigen as possible. A monoclonal antibody with inherently higher binding specificity for the marker/antigen may be used as a detection antibody for each specific isoform of SET.

Polyclonal antibodies are raised by injecting (e.g., subcutaneous or intramuscular injection) an immunogen into a suitable non-human mammal (e.g., a mouse or a rabbit). Generally, the immunogen should induce production of high titers of antibody with relatively high affinity for the target antigen. If desired, the marker may be conjugated to a carrier protein by conjugation techniques that are well known in the art. Commonly used carriers include keyhole limpet hemocyanin (KLH), thyroglobulin, bovine serum albumin (BSA), and tetanus toxoid. The conjugate is then used to immunize the animal. The antibodies are then obtained from blood samples taken from the animal. The techniques used to produce polyclonal antibodies are extensively described in the literature (see, e.g., Methods of Enzymology, "Production of Antisera with Small Doses of Immunogen: Multiple Intradermal Injections," Langone, et al. eds. (Acad. Press, 1981)). Polyclonal antibodies produced by the animals can be further purified, for example, by binding to and elution from a matrix to which the target antigen is bound. Those of skill in the art will know of various techniques common in the immunology arts for purification and/or concentration of polyclonal, as well as monoclonal, antibodies (see, e.g., Coligan, et al. (1991) Unit 9, Current Protocols in Immunology, Wiley Interscience).

Monoclonal antibodies (mAbs) may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified antifungal protein, polypeptide or peptide. The immunizing composition is administered in a manner effective to stimulate antibody producing cells. Rodents such as mice and rats are preferred animals, however, the use of rabbit, sheep, or frog cells is also possible. The use of rats may provide certain advantages but mice are preferred, with the BALB/c mouse being most preferred as this is most routinely used and generally gives a higher percentage of stable fusions.

In some embodiments, the SET-specific antibody recognizes a holoprotein or an antigen of both the α and the β isoform of SET. In these embodiments, the SET-specific antibody detects both isoforms of SET. In other embodiments, the SET-specific antibody of the invention recognizes a holoprotein or an antigen derived from the SET α isoform or the SET β isoform. SET α isoform-specific antibodies recognize a holoprotein or an antigen of the SET α isoform and do not recognize or bind to a holoprotein or an antigen of the SET β isoform. SET β isoform-specific antibodies recognize a holoprotein or an antigen of the SET β isoform and do not recognize or bind to a holoprotein or an antigen of the SET α isoform. The holoprotein or antigen derived from the SETα isoform or the SETβ isoform may be of SEQ ID NO: 1, SEQ ID NO: 2, SEQ ID NO: 3, or SEQ ID NO: 4.

In some embodiments, SET expression is measured by contacting a biological sample from a patient with an antibody that binds the SET protein (i.e., a SET-specific antibody that detects both the α and the β isoform), the SET α isoform (i.e., a SET α isoform-specific antibody), and/or the SET β isoform (i.e., a SET α isoform-specific antibody) and then detecting the presence or absence of a reaction product. The antibody may be monoclonal, polyclonal, chimeric, or a fragment of the foregoing and the step of detecting the reaction product may be carried out with any suitable immunoassay.

In one embodiment, SET expression levels are measured in an immunoassay with a biological sample, an antibody, and means for producing a detectable signal. The antibody can be immobilized on a support, such as a bead (such as protein A and protein G agarose beads), plate or slide, and contacted with the specimen suspected of containing the antigen in a liquid phase. The support is then separated from the liquid phase and either the support phase or the liquid phase is examined for a detectable signal employing means for producing such signal. The signal is related to the presence of the analyte in the sample. Means for producing a detectable signal include the use of radioactive labels, fluorescent labels, or enzyme labels. For example, if the antigen to be detected contains a second binding site, an antibody which binds to that site can be conjugated to a detectable group and added to the liquid phase reaction solution before the separation step. The presence of the detectable group on the solid support indicates the presence of the antigen in the test sample. Examples of suitable immunoassays include, but are not limited to oligonucleotides, immunoblotting, immunoprecipitation, immunofluorescence methods, chemiluminescence methods, electrochemiluminescence (ECL) or enzyme-linked immunoassays.

Those skilled in the art will be familiar with numerous specific immunoassay formats and variations thereof which may be useful for carrying out the method disclosed herein including enzyme linked immunosorbent assays (ELISAs), enzyme linked immunospot assay (ELISPOT), radioimmunoassays (RIA), radioimmune precipitation assays (RIPA), immunobead capture assays, Western blotting, dot blotting, gel-shift assays, flow cytometry, immunohistochemistry, fluorescence microscopy, protein arrays, multiplexed bead arrays, magnetic capture, in vivo imaging, fluorescence resonance energy transfer (FRET), and fluorescence recovery/localization after photobleaching (FRAP/FLAP). See generally E. Maggio, Enzyme-Immunoassay, (1980) (CRC Press, Inc., Boca Raton, Fla.); see also U.S. Pat. No. 4,727,022 to Skold et al. titled "Methods for Modulating Ligand-Receptor Interactions and their Application," U.S. Pat. No. 4,659,678 to Forrest et al. titled "Immunoassay of Antigens," U.S. Pat. No. 4,376,110 to David et al., titled "Immunometric Assays Using Monoclonal Antibodies," U.S. Pat. No. 4,275,149 to Litman et al., titled "Macromolecular Environment Control in Specific Receptor Assays," U.S. Pat. No. 4,233,402 to Maggio et al., titled "Reagents and Method Employing Channeling," and U.S. Pat. No. 4,230,767 to Boguslaski et al., titled "Heterogeneous Specific Binding Assay Employing a Coenzyme as Label."

Antibodies can be conjugated to a solid support suitable for a diagnostic assay (e.g., beads such as protein A or protein G agarose, microspheres, plates, slides or wells formed from materials such as latex or polystyrene) in accordance with known techniques, such as passive binding. Antibodies as described herein may likewise be conjugated to detectable labels or groups such as radiolabels (e.g., 35S, 125I, 131I), enzyme labels (e.g., horseradish peroxidase, alkaline phosphatase), and fluorescent labels (e.g., fluorescein, Alexa, green fluorescent protein, rhodamine) in accordance with known techniques.

The SET peptides disclosed herein can be used as binders in any of the assays herein described. For example, peptides corresponding to any of SEQ ID NOs: 1, 2, 3, or 4 may be used in any of the immunoassays described above. Immunoassays using peptides as binders have been previously described in U.S. Pat. Nos. 7,205,280; 7,319,092; 7,915,226; 8,198,234; and 7,947,645, each of which is incorporated herein by reference in its entirety.

In some embodiments, the level of SET expression is measured by quantifying SET mRNA. In some embodiments, the total SET mRNA is measured using PCR primers and probes that target SET mRNA that is common to both the α and the β isoforms of SET. In other embodiments, SET α isoform mRNA is detected using PCR primers and probes specific to the SET α isoform. In other embodiments, SET β isoform mRNA is detected using primers and probes specific to the SET β isoform. In some embodiments, one primer may be outside of the exon sequence. In some embodiments, the primer pair will amplify SET α isoform, even if only one primer is specific to the SET α isoform. In other embodiments, the primer pair will amplify SET β isoform, even if only one primer is specific to the SET β isoform. In some embodiments, SET α isoform mRNA is detected using PCR where one or both primers bind within an exon specific to the SET α isoform. In other embodiments, SET β isoform mRNA is detected using PCR where one or both primers bind within an exon specific to the SET β isoform. mRNA can be quantified by a variety of experimental techniques including quantitative PCR using primers to amplify SET mRNA and a nucleic acid probe targeting SET mRNA. Nucleic acid primers suitable for use in the invention may be from about 15 to about 30 bases in length. Nucleic acid probes suitable for use in the invention may be from about 20 to about 30 bases in length. Examples of nucleic acid primers and probes targeting SET mRNA are shown in Table 6 and include SET α isoform primers (e.g., SEQ ID NOs: 5 and 6), SET α isoform probes (e.g., SEQ ID NO: 7), SET β isoform primers (e.g., SEQ ID NOs: 8 and 9), SET β isoform probes (e.g., SEQ ID NO: 10), and SET primers that recognize both α and β SET isoforms (common SET primers, e.g., SEQ ID NOs: 11 and 12), and SET probes that recognize both α and β SET isoforms (common SET probes, e.g., SEQ ID NO: 13).

The most sensitive and most flexible quantitative method to measure SET mRNA is RT-PCR, which can be used to compare mRNA levels in different sample populations, in normal and tumor tissues, with or without drug treatment, to characterize patterns of gene expression, to discriminate between closely related mRNAs, and to analyze RNA structure.

The first step is the isolation of mRNA from a target sample. The starting material is typically total RNA isolated from human tumors or tumor cell lines, and corresponding normal tissues or cell lines, respectively. Thus RNA can be isolated from a variety of primary tumors, including breast, lung, colon, prostate, brain, liver, kidney, pancreas, spleen, thymus, testis, ovary, uterus, head and neck, etc., tumor, or tumor cell lines, with pooled DNA from healthy donors. Additional examples of cancer cell lines include those associated with chronic lymphocytic leukemia, B-cell non-Hodgkin's lymphoma, and melanoma. If the source of mRNA is a primary tumor, mRNA can be extracted, for example, from frozen or archived paraffin-embedded and fixed (e.g. formalin-fixed) tissue samples.

General methods for mRNA extraction are well known in the art and are disclosed in standard textbooks of molecular biology, including Ausubel et al., Current Protocols of Molecular Biology, John Wiley and Sons (1997). Methods for RNA extraction from paraffin embedded tissues are disclosed, for example, in Rupp and Locker, Lab Invest. 56:A67 (1987), and De Andres et al., BioTechniques 18:42044 (1995). In particular, RNA isolation can be performed using purification kit, buffer set and protease from commercial manufacturers, such as Qiagen, according to the manufacturer's instructions. For example, total RNA from cells in culture can be isolated using Qiagen RNeasy mini-columns. Other commercially available RNA isolation kits include MasterPure™ Complete DNA and RNA Purification Kit (EPICENTRE®, Madison, Wis.); and Paraffin Block RNA Isolation Kit (Ambion, Inc.). Total RNA from tissue samples can be isolated using RNA Stat-60 (Tel-Test). RNA prepared from tumor can be isolated, for example, by cesium chloride density gradient centrifugation.

As RNA cannot serve as a template for PCR, the first step in gene expression profiling by RT-PCR is the reverse transcription of the RNA template into cDNA, followed by its exponential amplification in a PCR reaction. The two most commonly used reverse transcriptases are avilo myeloblastosis virus reverse transcriptase (AMV-RT) and Moloney murine leukemia virus reverse transcriptase (MMLV-RT). The reverse transcription step is typically primed using specific primers, random hexamers, or oligo-dT primers, depending on the circumstances and the goal of expression profiling. For example, extracted RNA can be reverse-transcribed using a GeneAmp RNA PCR kit (Perkin Elmer, Calif., USA), following the manufacturer's instructions. The derived cDNA can then be used as a template in the subsequent PCR reaction.

Although the PCR step can use a variety of thermostable DNA-dependent DNA polymerases, it typically employs the Taq DNA polymerase, which has a 5'-3' nuclease activity but lacks a 3'-5' proofreading endonuclease activity. Thus, TaqMan® PCR typically utilizes the 5'-nuclease activity of Taq or Tth polymerase to hydrolyze a hybridization probe bound to its target amplicon, but any enzyme with equivalent 5' nuclease activity can be used. Two oligonucleotide primers are used to generate an amplicon typical of a PCR reaction. A third oligonucleotide, or probe, is designed to detect nucleotide sequence located between the two PCR primers. The probe is non-extendible by Taq DNA polymerase enzyme, and is labeled with a reporter fluorescent dye and a quencher fluorescent dye. Any laser-induced emission from the reporter dye is quenched by the quenching dye when the two dyes are located close together as they are on the probe. During the amplification reaction, the Taq DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data.

TaqMan® RT-PCR can be performed using commercially available equipment, such as, for example, ABI PRISM 7700™ Sequence Detection System™ (Perkin-Elmer-Applied Biosystems, Foster City, Calif., USA), or Lightcycler (Roche Molecular Biochemicals, Mannheim, Germany). In a preferred embodiment, the 5' nuclease procedure is run on a real-time quantitative PCR device such as the ABI PRISM 7700™ Sequence Detection System™. The system consists of a thermocycler, laser, charge-coupled device (CCD), camera and computer. The system amplifies samples in a 96-well format on a thermocycler. During amplification, laser-induced fluorescent signal is collected in real-time through fiber optics cables for all 96 wells, and detected at the CCD. The system includes software for running the instrument and for analyzing the data.

5'-Nuclease assay data are initially expressed as Ct, or the threshold cycle. As discussed above, fluorescence values are recorded during every cycle and represent the amount of product amplified to that point in the amplification reaction. The point when the fluorescent signal is first recorded as statistically significant is the threshold cycle (Ct).

To minimize errors and the effect of sample-to-sample variation, RT-PCR is usually performed using an internal standard. The ideal internal standard is expressed at a constant level among different tissues, and is unaffected by the experimental treatment. RNAs most frequently used to normalize patterns of gene expression are mRNAs for the housekeeping genes glyceraldehyde-3-phosphate-dehydrogenase (GAPDH) and 13-actin.

A more recent variation of the RT-PCR technique is the real time quantitative PCR, which measures PCR product accumulation through a dual-labeled fluorigenic probe (i.e., TaqMan® probe). Real time PCR is compatible both with quantitative competitive PCR, where internal competitor for each target sequence is used for normalization, and with quantitative comparative PCR using a normalization gene contained within the sample, or a housekeeping gene for RT-PCR. For further details see, e.g. Held et al., Genome Research 6:986-994 (1996).

According to one aspect of the present invention, PCR primers and probes are designed based upon intron sequences present in the gene to be amplified. In this embodiment, the first step in the primer/probe design is the delineation of intron sequences within the genes. This can be done by publicly available software, such as the DNA BLAT software developed by Kent, W. J., Genome Res. 12(4):656-64 (2002), or by the BLAST software including its variations. Subsequent steps follow well established methods of PCR primer and probe design.

In order to avoid non-specific signals, it is important to mask repetitive sequences within the introns when designing the primers and probes. This can be easily accomplished by using the Repeat Masker program available on-line through the Baylor College of Medicine, which screens DNA sequences against a library of repetitive elements and returns a query sequence in which the repetitive elements are masked. The masked intron sequences can then be used to design primer and probe sequences using any commercially or otherwise publicly available primer/probe design packages, such as Primer Express (Applied Biosystems); MGB assay-by-design (Applied Biosystems); Primer3 (Steve Rozen and Helen J. Skaletsky (2000) Primer3 on the WWW for general users and for biologist programmers. In: Krawetz S, Misener S (eds) Bioinformatics Methods and Protocols: Methods in Molecular Biology. Humana Press, Totowa, N.J., pp 365-386).

The most important factors considered in PCR primer design include primer length, melting temperature (Tm), and G/C content, specificity, complementary primer sequences, and 3'-end sequence. In general, optimal PCR primers are generally 17-30 bases in length, and contain about 20-80%, such as, for example, about 50-60% G+C bases. Tm's between 50 and 80° C., e.g. about 50 to 70° C. are typically preferred.

For further guidelines for PCR primer and probe design see, e.g. Dieffenbach, C. W. et al., "General Concepts for PCR Primer Design" in: PCR Primer, A Laboratory Manual, Cold Spring Harbor Laboratory Press, New York, 1995, pp. 133-155; Innis and Gelfand, "Optimization of PCRs" in: PCR. Protocols, A Guide to Methods and Applications, CRC Press, London, 1994, pp. 5-11; and Plasterer, T. N. Primerselect: Primer and probe design. Methods Mol. Biol. 70:520-527 (1997), the entire disclosures of which are hereby expressly incorporated by reference.

EXAMPLES

Example 1

SET Expression and Antagonism in CLL

Studies of a limited number of samples from CML patients and patients with other tumors have reported increased SET levels in isolated malignant cells. (Adachi et al. 1994) (Neviani et al. 2005) We sought to determine if the SET oncoprotein was overexpressed in CLL cells relative to normal B-cells and to quantify the effect of SET overexpression on parameters of disease. SET was significantly overexpressed in CLL cells and related non-Hodgkin's lymphoma (NHL) cell line cells. In freshly-isolated CLL patient samples, higher cellular levels of the SET correlated with more aggressive disease requiring earlier treatment. Antagonism of SET using shRNA-mediated knockdown or pharmacological antagonism with novel cell permeable SET antagonist peptides induced apoptosis, reduced cellular levels of Mcl-1, and caused death of CLL and NHL cells, but normal B-cells were scarcely affected by SET antagonism. In addition, pharmacological SET antagonism in vivo inhibited growth of B-cell NHL tumor xenografts in SCID mice.

Methods

All reagents were from Sigma-Aldrich unless noted otherwise. Anti-SET antibody was from Santa Cruz. Anti β-actin, total c-Myc, pS62 c-Myc, and Mcl-1 were from Abcam. All primary antibodies were used at a 1:1000 dilution, except for β-actin that was used at 1:10,000. All secondary antibodies are near-IR conjugated antibodies from Licor and were used at 1:10,000. All peptides were synthesized by PolyPeptide Laboratories (San Diego, Calif.) using standard FMOC-based chemistry with acetate at the N-terminus and amides at the C-terminus. Each peptide was >95% pure.

Normal B-Cell and CLL Cell Preparation.

CLL was diagnosed according to the NCl Working Group criteria (Hallek et al. 2008). Healthy volunteers and CLL patients from the Duke University and Durham Va. Medical Centers were enrolled in IRB-approved research protocols to collect clinical data and blood. Subjects gave signed informed consent prior to phlebotomy, in accordance with the Declaration of Helsinki. Blood was collected from participants into heparin-tubes, and CLL cells were purified as noted before (Weinberg et al. 2007). Briefly, CLL cells were isolated using the RosetteSep® B cell enrichment cocktail (catalog #15024/15064; Stem Cell Technologies, Vancouver, BC, Canada) according to the manufacturer's directions. This method yielded CLL cell purity of greater than 95% CD5+CD19+ B-cells as determined by flow cytometry. Normal B-lymphocytes were isolated using the EasySep® B-cell enrichment cocktail (catalog #15024/15064; Stem Cell Technologies, Vancouver, BC, Canada) according to the manufacturer's directions, with a purity of >94% CD 19+ lymphocytes.

IGVH mutation status, CD38 and ZAP70 expression, and interphase cytogenetics were determined as before (Weinberg et al. 2007). The length of time to initiation of treatment from the date of diagnosis was defined as the time-to-treatment (TTT). Individual physicians managing the patients made decisions regarding treatment initiation based on NCI Working Group criteria (Hallek et al. 2008). Some patients' treatments were started before being seen at the Durham Va. or Duke University Medical Centers. The length of time from diagnosis to death from any cause was defined as overall survival.

Quantitative PCR Measurement of SET mRNA.

Total RNA from CLL cell pellets was prepared using Qiagen's RNeasy Mini Kit (catalog #74104) following the manufacturer's protocol. cDNA was prepared using the High Capacity cDNA Reverse Transcription Kit (Applied Biosystems catalog #436881) following the manufacturer's protocol. Quantitative PCR was performed using TaqMan master mix and probes from Applied Biosystems and following manufacturer's protocol. Fold changes were calculated using $\Delta\Delta^{ct}$ method.

Western Blots.

Cells were lysed in NP40 buffer (50 mM Tris, 0.2% NP40, 150 mM NaCl) and the protein concentration of the lysate determined using the BCA assay (Hoane et al. 2007) and adjusted to 5 mg/mL total protein. Laemmli protein electrophoresis buffer (4×, 75 µL) was added to the cell lysate (25 µL), and the solutions were heated to 90° C. for 5 minutes. Protein solutions were loaded onto gels and separated by SDS PAGE, blotted onto nitrocellulose membranes (Bio-Rad). The nitrocellulose membranes were blocked using 5% nonfat milk in Tris-buffered saline containing 0.1% Tween 20 (TBST) for 3 hours, washed with TBST. The membrane was incubated overnight at 4° C. in the primary antibody of one species and a loading control (usually GAPDH) antibody of a second species diluted in SuperBlock. (Hoane et al. 2007) We washed membranes with TBST for 1 hour and incubated with the appropriate IRDye® 680 or IRDye® 800 secondary antibodies to detect the primary and loading control antibodies. The membranes were washed thoroughly and protein bands visualized and quantitated [Odyssey Infrared scanner (Li-Cor)].

Large Scale SET Quantification in CLL Patient Samples.

For immunoblot, analyses of SET on a larger number of samples, we used anti-I2PP2A (E-15) antibody from Santa Cruz Biotechnology, Inc. (Santa Cruz, Calif.). Frozen patient cells were lysed by freeze-thaw in Mammalian Protein Extraction Reagent (Pierce, Rockford, Ill.) with a protease inhibitor. We used lysates from a single stock of Ramos cells in each individual gel as a control for quantitation across all samples. Fifty µg lysate per lane was electrophoresed and blotted onto PVDF membranes. We used the reversible Ponceau protein staining method as a loading control across lanes. (Romero-Calvo et al. 2010) Briefly, after transfer, PVDF membranes were rinsed for 10 minutes in distilled water and incubated in 0.1% Ponceau S Solution (Sigma) for 10 minutes, followed by a brief rinse in distilled water. Membranes were imaged using a standard scanner and then rinsed further in distilled water and then in TBS-Tween 20 (0.1%) to eliminate the Ponceau stain. After blocking the membranes, we incubated them with antibodies. We processed the blots with an anti-goat IgG-horseradish peroxidase conjugate (Santa Cruz) and SuperSignal® West Femto Maximum Sensitivity Substrate (Thermo Scientific, Rockford, Ill.). Band densities were quantified and expressed as a ratio of SET band density/Ponceau band density (total proteins) and calculated relative to Ramos lysate SET (arbitrarily established as 100). We dichotomized SET "high" and "low" values using the following cutoffs: SETα 70.3 units, SET β 115 units, total SET (α+β) 74.5 units, and SET α/β ratio of 0.78 units relative to the Ramos cell control.

shRNA Mediated SET Knockdown.

Lentivirus-expressing shRNA for SET and a non-coding control were from Santa Cruz Biotechnology. Cells ($5\times10^5$/mL) were seeded into 12 well cell culture plates (1 mL/well) in RMPI-1640 media. Polybrene (1 µL, Santa Cruz) and lentivirus (10 µL) were added to each well, and the plate was spun at 1500 rpm for 1 hour at room temperature. The plate was then placed at 37° C. for 2 hours. Cells were then seeded into 6 well plates, and 2 mL normal growth media was added per well. We treated cells 48 hours after transduction and then harvested 72 hours after transduction for assays and Western blotting.

PP2A Activity Measurement.

Cultured 32D:BCR/Abl CML cells were grown in standard media, treated as indicated, and lysed in NP40 buffer. The protein concentration (Hoane et al. 2007) was adjusted to 2 mg/mL protein, and 500 µg of protein was combined with 4 µL of anti-PP2A antibody (1D6, Upstate) and 50 µL of protein-A-agarose beads in 500 µL. The mixture was shaken for 2 hr at 4° C. and then beads were collected by centrifugation. Following four washes, 50 µL of phosphatase assay buffer (Upstate) was added to the beads, vortexed, and 50 µL of the bead slurry was added to one well of a 96 well plate. A 10 mM stock of 6,8-difluoro-4-methylumbelliferyl phosphate (DiFMUP, Invitrogen) was diluted to 100 µM in assay buffer, and 50 µL was added to each well. Fluorescence intensity of the product of cleavage of phosphate from DiFMUP (a synthetic phosphatase substrate) was measured using a plate reader every 3 minutes, with shaking every 30 seconds over a 30 minute period. Specificity of the phosphatase assay for PP2A was assessed by incubating the immunoprecipitated protein with 25 nM oakadaic acid (OA), a concentration that selectively inhibits PP2A. Data presented represent the phosphate release of a sample with the background level of phosphate release of the OA-inhibited control subtracted.

Affinity Purification of SET Using Biotin Labeled COG Peptides.

CLL cells were lysed in NP40 buffer (50 mM Tris, 0.2% NP40, 150 mM NaCl) by a single freeze thaw cycle. Lysate protein concentration was adjusted to 5 mg/mL. Streptavidin agarose beads (1 mL) were washed with 10 mL of NP40 buffer, and 0.5 mL of beads was added to 1 mL of extract. ABeads were then collected by filtration through a disposable mini-column (Bio-Rad), and the flow-through extract was collected for analysis. Following washing with 100 mL of chilled NP40 buffer, the beads were removed from the column, collected by centrifugation, and 75 µL of 4× Laemmli buffer was added. Beads were vortexed and heated to 90° C. for 10 min to ensure that all proteins were released from the beads. Proteins were separated by SDS PAGE and Western blotting was used to determine if the COG133 and COG112 peptides bound to both isoforms of SET from a CLL patient sample.

Annexin-V:Propidium Iodide Assay for Apoptosis.

Apoptosis was measured using the Annexin apoptosis detection kit (BD Biosciences-Pharmingen) according to the manufacturer's instructions. (Levesque et al. 2008) Briefly, COG-treated or untreated cells were stained with Annexin V-FITC- and propidium iodide for 15 minutes in 1×binding buffer (10 mM HEPES, pH 7.4, 140 mM NaCl, 2.5 mM $CaCl_2$) and analyzed by flow cytometry using a FACSCalibur instrument (BD Biosciences). Data were analyzed using CellQuest 3.3 software (BD Biosciences).

CLL Cell Culture/Cytotoxicity Assays.

For cytotoxicity assays, $3\times10^6$ CLL cells/well were cultured in 24 well tissue culture plates in 1.5 mL of Hybridoma SFM™ (Gibco, Long Island, N.Y.) as described by Levesque et al. (Levesque et al. 2001) (Levesque et al. 2003) All cultures were incubated at 37° C., 5% $CO_2$ in air. Compounds were applied to CLL cells ($0.25\times10^6$ cells/well in a 96 well plate) and after 72 hours, viable cells were assessed using the MTS assay (Pharmacia) to determine the concentration of COG compound that was effective in displaying 50% cytotoxicity for the CLL cells (ED50). (Levesque et al. 2003)

Xenograft Model of Tumor Growth Suppression.

Female SCID mice (6-8 weeks old) were injected subcutaneously on left flank with $10^7$ Ramos cells in 200 µL PBS. Mice were monitored daily for tumor growth by palpation. When tumors became large enough for caliper measurement, tumor volumes were calculated as (length times width$^3$)×0.5 as described by Schliemann et al. (Schliemann et al. 2009) Once tumors reached 50-100 mm$^3$, we randomly assigned mice to two groups, with approximate equalization of tumor volumes between groups. COG449 (5 mg/kg) or a vehicle control was administered by daily subcutaneous injection (5 mL/kg injection volume). At the end of experiment, tumors were dissected, photographed, and wet weights of each tumor were measured.

Statistical Analysis.

If quantitative data were normally distributed, single comparisons between groups were made by Student's t test; if not, log transformation or non-parametric Mann-Whitney testing was used. When multiple comparisons were made between groups, the data were analyzed using two way ANOVA with the Newman-Keuls post-test. Kaplan-Meier curves were used to graphically display overall survival and time to treatment relative to SET levels. Statistical significance for time to treatment and overall survival was analyzed using the proportional hazards regression and chi square tests, using an alpha of 0.05.

Results

Figure 1:
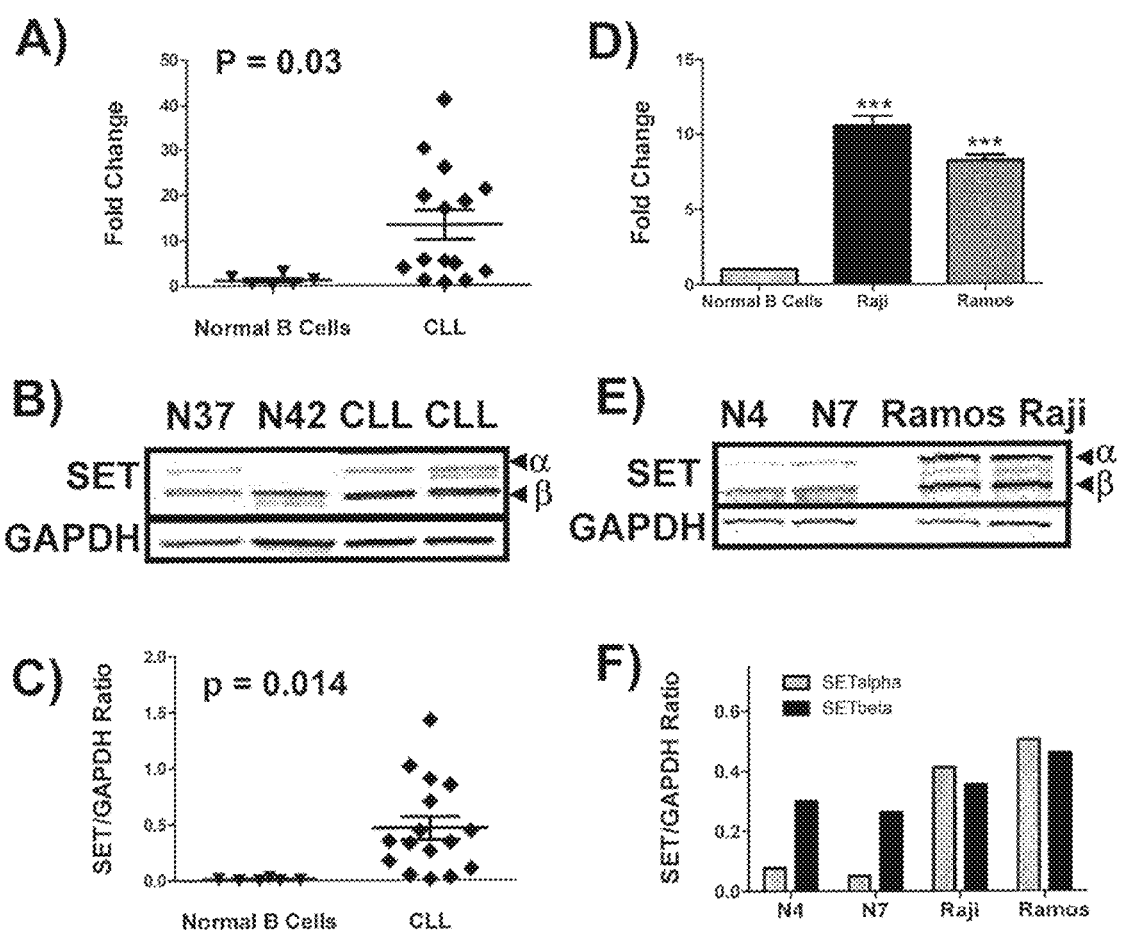
FIG. 1: SET is overexpressed in CLL and NHL. (A) mRNA was isolated from 15 CLL patients and 6 normal B-cell samples and SET mRNA was quantified by qPCR. (B) Representative immunoblot of two normal B-cell (N37 and N42) and two CLL cell extracts showing overexpression of both the α- and β-isoforms of SET as indicated in the CLL cells. (C) SET/GAPDH protein ratios measured for 16 CLL patients and 6 normal B-cell samples used in A, showing a significant increase in expression of SET mRNA in B-CLL cells relative to normal B-cells. (D) SET mRNA levels from two normal B-cell samples and Raji and Ramos cells quantified by qPCR. (E) Immunoblotting of two normal B-cell (N4 and N7) and Raji and Ramos cell extracts. While SET levels appear higher in the normal samples, it is due to higher intensity settings for this blot than normal shown compared to the CLL samples in B. (F) Quantitation of the α- and (β-isoforms of the SET protein (normalized to GAPDH) for Raji and Ramos NHL cell lines showing that the major increase in SET levels is due to increased α-isoform expression.

We isolated mRNA from freshly prepared B-CLL cells from patients and normal B-cells from healthy volunteers, and determined SET mRNA levels by quantitative RT-PCR (qPCR). SET mRNA levels were 11.2±2.7 fold higher in CLL cells than the mean of the normal B-cells (p=0.03) (FIG. 1A). Immunoblots from these same samples using an anti-SET antibody demonstrated that both the 290 amino acid α-isoform (accession #NP_001116293) and the 277 amino acid β-isoform (accession #NP_003002) that arise from alternative splicing were higher in the CLL cells than in normal B-cells (FIG. 1B). The total SET (α+β) values were higher in CLL cells (0.048±0.004) than in normal B cells (0.010±0.003) (p=0.014) (FIG. 1C). We also evaluated SET expression in the Raji and Ramos cell lines of human B-cell NHL. Unlike CLL cells, these cells proliferate rapidly in vitro and can be more easily genetically manipulated by lentiviral transduction. SET mRNA in Raji cells was 10.5±0.7 fold higher than in normal B-cells, and 8.2±0.4 fold higher in Ramos cells (p=0.0002) than in normal B-cells (FIG. 1D), which was similar to the overexpression levels observed in the CLL samples. Immunoblot analysis revealed elevated levels of SET protein in both Raji and Ramos cells relative to normal B-cell extracts (FIG. 1E). Similar to the CLL cells, both the α- and β-isoforms of SET were overexpressed in the NHL cell lines to comparable degrees, while the 277 amino acid β-isoform was more prominent than the α-isoform in normal B-cell samples (FIG. 1F).

To determine if SET levels were indicative of more rapid CLL disease progression, we used Western blotting to quantify the levels of each isoform of the SET protein in cell extracts from 285 patients. Patients were selected for this study based on the availability of stored samples from first diagnosis and patient history. Detailed patient information is given in Table 1.

high and low levels of the β-isoform of SET showed more rapid progression (shorter TTT) in patients with high SETβ (FIG. 2A), but this was not statistically different. However, patients with high SETα (p=0.0004; FIG. 2B), high total (α+β) SET (p=0.0005; FIG. 2C), and a high α/β ratio had statistically significantly shorter TTT (p=0.019; FIG. 2D) indicating that higher SET levels correlated with more rapid progression as signified by the earlier need for therapeutic intervention. The TTT values and statistical parameters are given in Table 2. Patients with elevated SET levels were more likely to have received treatment (n=140) for the disease than

TABLE 1

Patient clinical features.

| | | | |
|---|---|---|---|
| Age at diagnosis [median (IQR$^a$)] | 60 (range 52-67) years | | n = 285 |
| Men & women | 193 (68%) men | | n = 285 |
| | 92 (32%) women | | |
| VA & Duke patients | 79 (28%) VA | | n = 285 |
| | 206 (72%) Duke | | |
| Race | 27 Black (10%) | | n = 271$^b$ |
| | 244 Caucasian (90%) | | |
| Rai stage: 0 | 161 (57%) | | n = 281 |
| 1 | 73 (26%) | | |
| 2 | 25 (9%) | | |
| 3 | 7 (2%) | | |
| 4 | 15 (5%) | | |
| Treatment history: untreated | 145 (51%) | | n = 285 |
| treated | 140 (49%) | | |
| CD38 expression | 220 negative (78%) | | n = 281 |
| | 61 positive (22%) | | |
| Zap70 expression | 126 negative (49%) | | n = 259 |
| | 133 positive (51%) | | |
| IGVH mutation status | 114 unmutated (44%) | | n = 261 |
| | 147 mutated (56%) | | |
| Cytogenetics | Normal | 41 (18.5%) | n = 222 |
| | 13q del$^c$ | 129 (58.1%) | |
| | 13q del only | 89 (40.1%) | |
| | Trisomy 12$^c$ | 38 (17.1%) | |
| | Trisomy 12 only | 30 (13.5%) | |
| | 17p del$^c$ | 31 (14.0%) | |
| | 17p del only | 9 (4.1%) | |
| | 11q del$^c$ | 33 (14.9%) | |
| | 11q del only | 8 (3.6%) | |
| | 2 abn. | 41 (18.5%) | |
| | 3 or more abn. | 4 (1.8%) | |
| Length of follow-up (median, IQR) | 6.0 (3.2-9.8) years | | n = 285 |
| Treated during the course of disease | 140 (49%) | | n = 285 |
| Died | 66 (23%) | | n = 285 |

Figure 2:
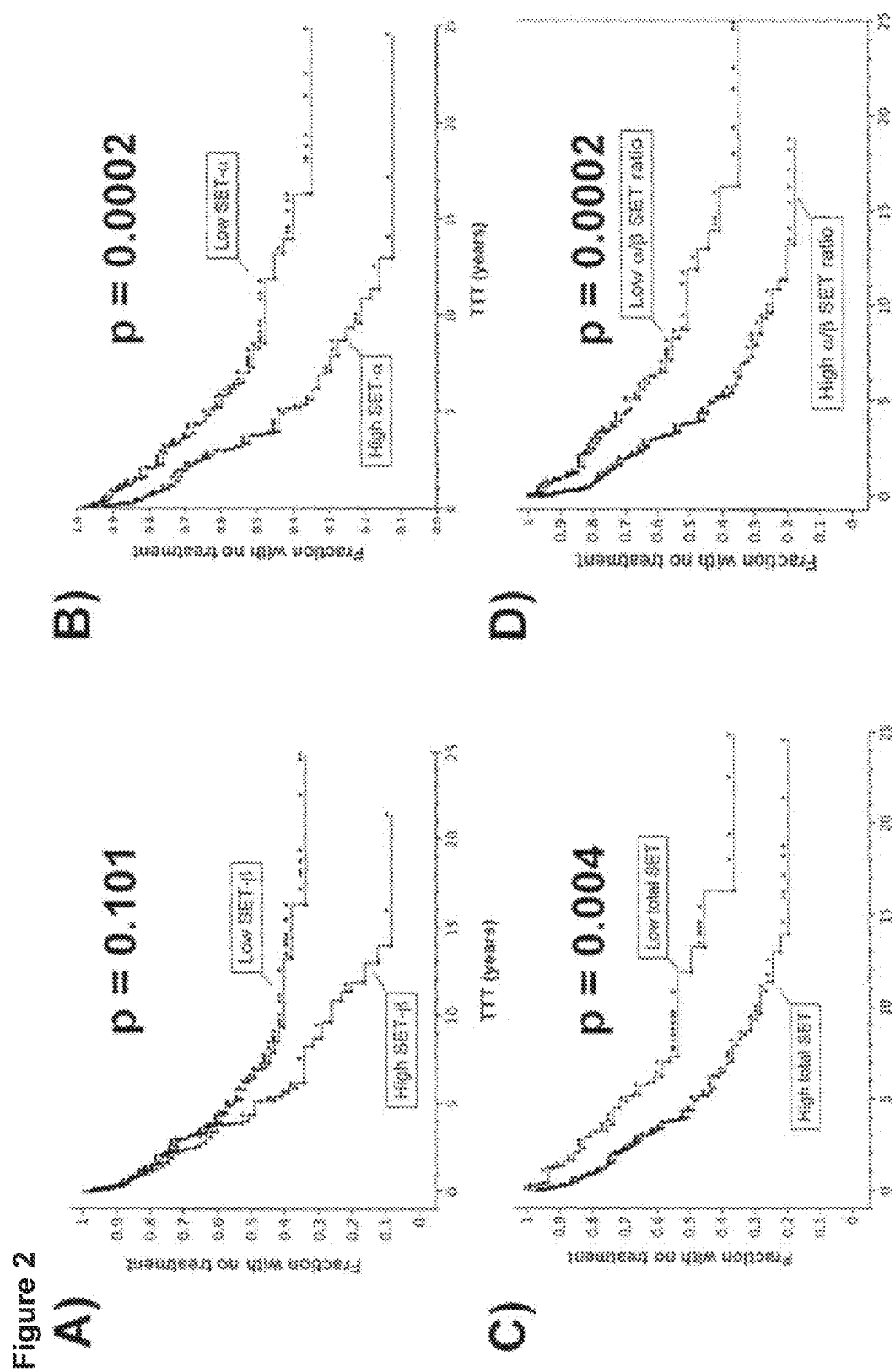
FIG. 2: Cellular SET protein levels correlate with parameters of CLL progression. The time from diagnosis to first needed treatment (the time to treatment; TTT) was assessed relative to SET protein levels in CLL cells as determined by quantitative immunoblotting. Patients with high levels of SET were compared to those with low levels of SET for (A) the β-isoform, (B) the α-isoform, (C) total (α+β) SET, and (D) the numerical ratio of the α-isoform and β-isoform (α/β ratio) (n=285). Those with high SETα, high total SET (α+β, and high α/β ratios had statistically significantly shorter TTT. The overall survival (OS) for patients with high levels of SET were compared to those with low levels of SET for (E) SETβ, (F) SETα, (G) total SET (α+β), and (H) the numerical ratio of the α-isoform and β-isoform (α/β ratio) (n=285). The OS was significantly shorter in patients with high α/β ratios of the SET isoforms (n=285).
Figure 2:
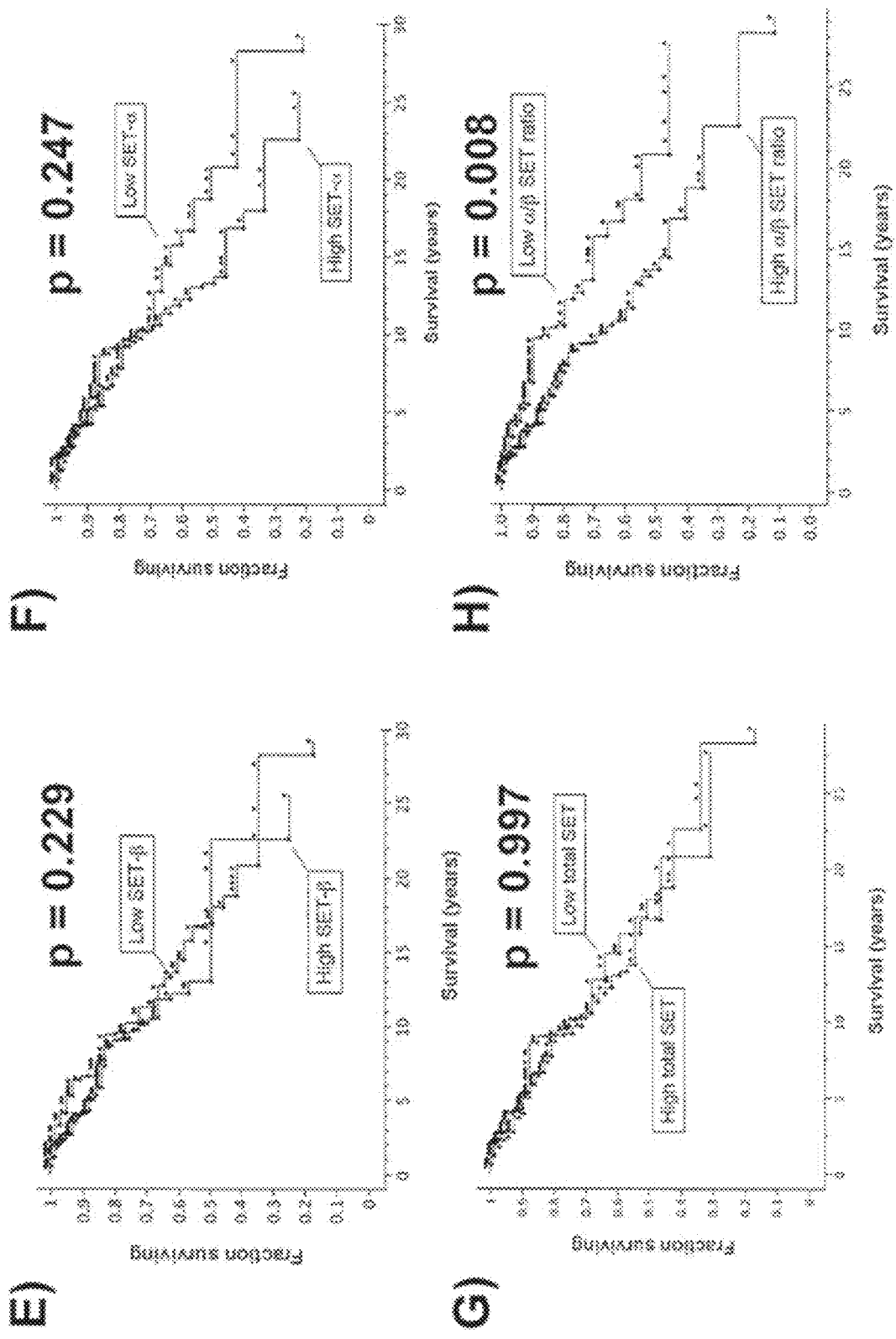

$^a$Interquartile range (25$^{th}$ to 75$^{th}$ percentile)
$^b$Not all analyses were performed on samples from each patient
$^c$denotes patients with this abnormality and these patients may have multiple abnormalities We used Kaplan-Meier curves to display differences in time to first treatment (TTT) and overall survival relative to SET levels (FIG. 2). Analysis of the TTT for the patients with the patients who had not received treatment (n=145) for SETα (p=0.004), for total α+β SET (p=0.015), and for α/β ratio (p=0.0001).

TABLE 2

Correlation values of SET protein isoform immunoblot densities with CLL prognostic parameters

| | Rai Stage$^a$ n = 281 | CD38$^b$ n = 285 | IGVH$^b$ n = 284 | Zap-70$^b$ n = 262 | 17p del$^b$ n = 31$^c$ | 13q del$^b$ n = 129$^c$ | 11q del$^b$ n = 33$^c$ | Trisomy 12$^b$ n = 38$^c$ |
|---|---|---|---|---|---|---|---|---|
| SET β-isoform | 0.173$^a$ | 0.289 | 0.347 | 0.405 | 0.632 | 0.705 | 0.810 | 0.881 |
| SET α-isoform | 0.017 | 0.161 | 0.0006 | 0.142 | 0.183 | 0.318 | 0.684 | 0.523 |
| Total SET (α + β) | 0.033 | 0.877 | 0.007 | 0.483 | 0.456 | 0.813 | 0.762 | 0.803 |
| α/β ratio | 0.598 | 0.004 | 0.002 | 0.193 | 0.620 | 0.087 | 0.837 | 0.177 |

$^a$p value by ANOVA
$^b$p value by Wilcoxson; chi squared
$^c$n = 222 total with cytogenetic determinations When performing a similar analysis to compare SET levels with overall survival (OS), patients with high and low levels of the SETβ, SETα and total SET (α+β) showed no significant difference in OS (FIGS. 2E, 2F, and 2G). However, patients with high α/β ratios had significantly different OS than patients with low ratios of the two isoforms (p=0.0005; FIG. 2H) with differences in median survival indicated in Table 3. CLL patients with high α/β ratios had significantly shorter OS than did patients with low α/β ratios where median survival was 4.1 years shorter in the group with higher α/β ratios (Table 3) (p=0.008). We also analyzed whether elevated SET levels (SETβ, SETα and total SET (α+β) and α/β ratios) correlated with known prognostic factors including Rai stage, CD38 expression, IGVH mutational status, Zap-70 expression and cytogenetic abnormalities (Table 3). We found that elevated SETα and total SET (α+β) levels correlated with increasing Rai stage (p values given in Table 2). Elevated SET α/β ratios correlated significantly with CD38 expression and elevated SETα, total SET (α+β), and α/β ratios correlated significantly with IGVH mutational status. No significant correlations were observed between SET expression levels and Zap-70 expression or cytogenetic abnormalities. Lack of correlation with cytogenetic abnormalities could relate in part to low numbers of patients in the cytogenetic abnormality subgroups.

1 µM increased the activity of PP2A in these cells to a greater level than did 5 µM FTY720 (FIG. 5B), a PP2A activator reported by Neviani et al. (Neviani et al. 2007).

Based on the increased activity of PP2A following SET antagonism using COG449, we evaluated the induction of apoptosis in primary CLL cells following treatment with COG449. CLL cells from seven patients were treated with COG449 or medium control for 2 hours. After treatment, cells were stained with Annexin-V and propidium iodide and analyzed by flow cytometry. We observed a dose dependent increase in Annexin-V/propidium iodide staining with an ED50 of 330 nM (FIG. 5C). To analyze the modulation of anti-apoptotic proteins in CLL cells, we measured the effect of COG449 treatment on the anti-apoptotic Bcl-2 family member Mcl-1 and observed a dose dependent decrease in the cellular level of Mcl-1 (FIG. 5D).

Based on the induction of apoptosis in CLL cells, we tested several analogs of COG449 for cytotoxicity against CLL cells freshly isolated from a number of patients and against normal B-cells from healthy volunteers (Table 4). Cells were cultured with the agents for 72 hours, and the viable cells were assessed for cytotoxicity using the MTS assay. COG445 was cytotoxic to CLL cells isolated from patients with an ED50 of 110 nM (FIG. 6A). In stark contrast, the EC50 for cytotoxicity in the B-cells from normal volunteers was found to be

TABLE 3

Time to treatment and overall survival parameters relative to specific SET protein isoform expression

| | Time to treatment (years) | | | Overall survival (years) | | |
|---|---|---|---|---|---|---|
| | High expression | Low expression | p value[a] | High expression | Low erpression | p value[a] |
| SET β-isoform | 4.3[b] (3.7-6.2[c]) | 6.4 (4.5-9.3) | 0.101 | 13.1 (11.3-) | 16.9 (13.7-28.2) | 0.229 |
| SET α-isoform | 3.8 (3.0-5.2) | 8.3 (5.8-16.3) | 0.0002 | 13.3 (11.3-22.6) | 20.6 (14.5-) | 0.247 |
| Total SET (α + β) | 4.3 (3.7-6.2) | 11.9 (5.8-) | 0.004 | 18.0 (12.3-28.3) | 16.7 (12.7-) | 0.997 |
| α/β ratio | 3.8 (3.1-5.2) | 11.9 (6.3-) | 0.0002 | 16.7 (10.6-22.6) | 20.8 (15.8-) | 0.008 |

[a]Determined by proportional hazards method
[b]Median
[c](5th to 95th percentile)

We have previously described peptide antagonists of SET that activate PP2A and lead to dephosphorylation of Akt and the p38 MAPK (Christensen et al. 2011). We confirmed that these peptides bound to both isoforms of SET in cell lysates from CLL samples (FIG. 3). CLL cells generally do not proliferate in vitro, and they are difficult to transfect. Therefore, we measured PP2A activity in 32D:BCR/Abl, cells with elevated SET levels and suppressed PP2A activity. (Neviani et al. 2005) We infected these cells with lentivirus encoding a SET-specific shRNA or a control non-coding lentivirus and confirmed reduction of SET by Western blotting (FIG. 4). Cells infected with a control lentivirus were treated with COG449 (a dimerized derivative of COG112 (Li et al. 2006) (Singh et al. 2008)) or a vehicle control and PP2A activity was measured. SET antagonism with either SET-shRNA or COG449 increased the activity of PP2A relative to controls (FIG. 5A). Furthermore, we found that COG449 treatment at nearly 2-log units higher at ≥10,000 nM. Similarly, COG449 was cytotoxic with an ED50 of 103 nM (FIG. 6B). We also analyzed the effect of shRNA-mediated knockdown of SET on the growth of B-cell lymphoma cell lines. Knockdown of SET in Raji cells following infection with a SET-specific shRNA lentivirus resulted in a reduction of SET levels by approximately 50% (FIG. 6C). This SET knockdown reduced the growth after 72 hours (p=0.009) (FIG. 6D). Antagonism of SET with COG449 also inhibited growth of Raji and Ramos NHL cells in vitro (FIGS. 6E, F). To determine if this cytotoxicity was modulated by PP2A, we treated Ramos cells with 1 nM OA (PP2A inhibitor) and found that this concentration of OA was not cytotoxic. However, treatment of the Ramos cells with 1 µM COG449 produced a robust cytotoxic effect that could be partially counteracted by treatment with OA (FIG. 7).

TABLE 4

Cytoxicity of COG compounds for CLL cells

| Compound | Sequence | CLL ED50 (µM) | Normal ED50 (µM) |
|---|---|---|---|
| COG056 (reverse 133) | LLRKRLKRLHSALRVRL | 12.9 ± 4.6 | >20 |
| COG133 | LRVRLASHLRKLRKLL | 4.4 ± 1.5 | >20 |

TABLE 4-continued

Cytoxicity of COG compounds for CLL cells

| Compound | Sequence | CLL ED50 (μM) | Normal ED50 (μM) |
|---|---|---|---|
| COG1410 | AS(Aib)LRKL(Aib)KRLL* | 5.7 ± 3.0 | >20 |
| COG112 | RQIKIWFQNRRMKWKK-C-LRVRLASHLRKLRKRLL | 1.4 ± 0.7 | >20 |
| COG445 (disulfide linked COG112) | RQIKIWFQNRRMKWKK-C-LRVRLASHLRKLRKRLL<br>\|<br>RQIKIWFQNRRMKWKK-C-LRVRLASHLRKLRKRLL | 0.11 ± 0.08 | >10 |
| COG449 (BMOE** linked COG112) | RQIKIWFQNRRMKWKK-C-LRVRLASHLRKLRKRLL<br><bmoc><br>RQIKIWFQNRRMKWKK-C-LRVRLASHLRKLRKRLL | 0.10 ± 0.01 | >10 |

*Aib = aminoisobutyric acid
**BMOE = bismaleimidoethane

Based on the cytotoxicity of SET antagonism in vitro, we sought to determine if pharmacological antagonism of SET with COG449 could reduce growth of cancerous B-cells in vivo using a murine model. To determine if the transgenic TCL-1 model (Johnson et al. 2006) was a good candidate for testing of SET antagonist peptides, we isolated malignant CD5+ cells from the spleen of a TCL-1 mouse and performed Western blotting to determine if SET was overexpressed in these mice. We found that unlike human CLL cells, SET was not overexpressed in the TCL-1 mouse leukemia-like cells (FIG. 8). Therefore, we used a murine xenograft model with human Ramos NHL cells that overexpress SET. Female SCID mice were subcutaneously injected with $10^7$ cells into the left flank, and tumor growth was monitored daily by palpation and caliper measurement until tumors reached approximately 150 mm³ on day 11. Mice were randomly assigned to two groups so that initial tumor size was approximately equal between groups. Daily treatment with COG449 (5 mg/kg, subcutaneous injection into the right shoulder area) or a vehicle control was initiated and measurements were performed by an experimenter who was blinded to the treatment agents (FIG. 9A). At day 19 (a time when control tumor volume reached maximum volume allowed for humane reasons) mice were euthanized. Tumors were dissected, weighed (FIG. 9B), photographed (FIG. 9C), and segmented for pathological examination. Statistical analysis by two way ANOVA indicated that tumor growth was significantly inhibited by COG449 (p=0.0008) and final tumor mass was significantly lower in COG449 treated animals (p=0.0009, t-test). Disaggregated cells from one portion of the tumors were analyzed by flow cytometry, and shown to be human B-cells.

SET overexpression was also observed in tumor samples from patients with breast cancer, prostate cancer, pancreatic cancer, ovarian cancer, and melanoma (FIGS. 10-14).

Example 2

The Prognostic Power for CLL Patients is Enhanced by Combining SET α/β Ratios with Other Prognostic Factors.

Based on the data showing that high ratios of α/β SET correlated with poorer overall survival and shorter time to treatment, we performed additional analysis of our patient cohort to determine if SET levels can also be used in conjunction with additional prognostic factors to identify patients with more aggressive disease.

Among the patients carrying mutated immunoglobulin-VH (IGVH) gene, there was significantly longer overall survival and TTT than patients with unmutated IGVH (p<0.0001; FIGS. 15A, B). This is consistent with other reports of mutated IGVH patients having a better prognosis than those with unmutated IGVH [Damle, 1999, Mamblin, 1999]. Importantly, we found that among patients with mutated IGVH, patients with high α/β ratios had significantly different TTT than patients with low ratios of the two isoforms (p.<0.0001; FIG. 16A). Significant results were also obtained when analyzing overall survival in the IGVH mutated group with high and low SET α/β ratio groups (p<0.0001; FIG. 16B). In addition to mutational status, we analyzed patients with low CD38 expression, another group with a good prognosis [Ibrahim, 2001]. In this patient group, patients with a high SET α/β ratio had significantly different median TTT (3.9 years) than patients with a low SET α/β ratio (12.3 years, p<0.0001). Similarly, patients with a high SET α/β ratio had significantly different overall survival (median time to death 16.9 years) than patients with a low SET α/β ratio (median time to death unreached; p<0.005; FIG. 17) A similar finding was also obtained for patients with high zeta-chain-associated protein kinase 70 (ZAP-70) expression [Rassenti, 2004]. Taken together, these data demonstrated that 1) the oncoprotein SET was overexpressed in CLL patient samples, 2) patients with higher SET α/β ratios had a shorter TTT and shorter overall survival than patients with lower SET α/β ratios, and 3) the prognostic power for CLL patients is enhanced by combining SET α/β ratios with other prognostic factors. However, no rapid method for determination of the α/β ratio exists in current clinical diagnostic labs.

Example 3

SET Isoform-Specific Antibodies and SET Isoform-Specific PCR Primers

We completed a test to determine if it was feasible to generate isoform specific antibodies. This was accomplished by synthesizing a peptide corresponding to the unique N-terminal region of SETα (sequence=MAPKRQSPLP-PQKKKPRP-C; SEQ ID NO: 2) with a cysteine incorporated at the C-terminus of this peptide. The peptide was then coupled by maleimide chemistry to keyhole limpet hemocyanin (KLH) and used to inoculate two rabbits that had been prescreened in dot blots for immunoreactivity to the peptide antigen. The rabbits were boosted with the KLH-antigen at 4 weeks and serum was obtained at 6 weeks. Dot blots performed with the peptide antigen immobilized on a nitrocellulose membrane followed by Dot-blotting as described below.

We found that the anti-SETα immunized rabbits produced positive sera that did not react with a control peptide immobilized on the membrane (FIG. 18). The antibodies from each of the two rabbits were designated COG16 and COG17. Final confirmation of selectivity of the antibodies from the SETα immunized rabbits was demonstrated by completing Western blotting with a Ramos cell lysate. We used the Ramos cell line lysate because it expresses high levels of both the SETα and SETβ isoforms and was used as our control in quantification of SET levels in the CLL patient samples [Longo, 2008]. When compared with a commercial goat antibody that recognizes both isoforms of SET, we found that the SETα selective sera recognized only the band that corresponded to the higher molecular weight SETα isoform (FIG. 19A). Further confirmation of the selectivity was obtained by repeating Western blots with Ramos lysate using either the selective SETα sera alone or sera that had been preincubated with the peptide that was used for the immunization as the detection antibody. This showed that the preincubation of the sera with the antigen peptide could eliminate the ability of the antibody to recognize the SETα protein on the blot (FIG. 19B). These results demonstrated the development of isoform selective antibodies that recognized unique isoforms of SET.

To develop the polyclonal SETα specific antibodies, we used the 19 amino acid peptide MAPKRQSPLP-PQKKKPRP-C (SEQ ID NO: 2) that matched the N-terminal 18 residues of the SETα isoform from the total unique sequence of the SET as shown in Table 5. This antigen was selected based on the Kyte-Doolittle Hydrophobicity scale [Liu, 2004], which has been used to design the SETβ antigen listed in Table 5.

TABLE 5

Sequences of SET and designed antigens

| Isoform | Identity | Sequence | SEQ ID NO. |
|---|---|---|---|
| SETα | Holoprotein | MAPKRQSPLPPQKKKPRPPPALGPEE TSASAGLPKKG*EKEQQEAIEHIDE* | 1 |
| | Antigen | MAPKRQSPLPPQKKKPRP | 2 |
| SETβ | Holoprotein | MSAPAAKVSKKELNSNHDGADETS*EK EQQEAIEHIDE* | 3 |
| | Antigen | KELNSNHDGADETS | 4 |

To verify staining of the selective SET alpha antibody (designated COG16, labeled with DyLight-648, red fluorescence probe) and a total SET antibody (Santa Cruz goat anti-SET labeled with DyeLight-488), the following protocol was employed.

To coat coverslips with PDL, 12 mm circular coverslips were washed with EtOH and allowed to dry, then transferred to a 24 well plate. 250 ul of 10 ug/ml PDL was added to each well and incubated at room temperature overnight. Excess PDL was removed, and coverslips were allowed to dry. Dry coverslips were stored at 4° C. PDL coated coverslips were placed in a 24 well plate and washed 1× with PBS. MDA-MB-231 cells were lifted with trypsin and counted. 50000 cells in 500 ul growth media was placed on each coverslip and allowed to adhere overnight. Cells were washed 1× with PBS and coverslips moved into a clean well. 200 ul 4% Pfa (PBS) was added for 15 min, then cells were washed 1× with 500 ul PBS. 500 ul Blocking buffer (PBS+10% BSA and 0.1% Triton-X100) was added for 30 min. Cells were washed 1× with PBS. Antibodies were diluted in blocking buffer (COG17 1:5, Santa Cruz total SET 1:10) and 200 ul per well was added and incubated for 2 hours, protected from light, then washed 5 times with 500 ul PBS. 1 drop of gold anti-fade was added. Coverslips were placed facedown into mounting media, avoiding air bubbles. Mounting media was allowed to solidify for at least 2 hours. Slides were then cleaned and imaged.

The results of the study are shown in FIG. 20. Total SET staining of MDA-MB-231 cells is showing in FIG. 20A (20×) and 20B (100×). COG 17 (SET alpha-specific) staining of MDA-MB-231 cells is shown in FIG. 20C (20×) and 20D (100×). Co-staining with both the total SET antibody and COG17 is shown in FIG. 20E (20×) and FIGS. 20F-20I (100×).

In addition, we generated primers and probes in order to amplify and detect the alpha and beta isoforms of SET by quantitative PCR. The primers and probes used for SET alpha, SET beta and SET common (which is designed to detect both alpha and beta isoforms) are shown in Table 6. As shown in FIG. 21, SET-1 alpha was specifically detected in the SET alpha control plasmid, whereas SET beta was specifically detected in the SET beta control plasmid. These data verified that the isoforms could be differentially detected by quantitative PCR.

TABLE 6

SET-qPCR primers and probes

| | Sequence | Color | SEQ ID NO |
|---|---|---|---|
| SET-1alpha f | AGA AGA AAC CAA GAC CAC CTC CTG | | 5 |
| SET-1alpha b | GTG TTC AAT CGC TTC TTG CTG TTC | | 6 |
| SET-1alpha PROBE | TGC AGG CTT GCC GAA GAA GGG AGA AA | JOE | 7 |
| SET-1beta f | CGG CGG CCA AAG TCA GTA AA | | 8 |
| SET-1beta b | GTG TTC AAT CGC TTC TTG CTG TTC | | 9 |
| SET-1beta PROBE | AAG GAG CTC AAC TCC AAC CAC GAC G | FAM | 10 |
| SET-1common f | CCA TCT TCG AAG TCC ACC GAA ATC | | 11 |
| SET-1common b | GCC TCT TCC TGC TGG CTT TAT T | | 12 |
| SET-1common PROBE | GGA TTT GAC GAA ACG TTC GAG TCA AAC GCA | FAM | 13 |

Quantitative PCR was performed on biological samples from CLL patients using the PCR primers and probes described above. Ramos cells were used as a positive control. The raw data across all patients tested is shown in Table 7. SET alpha isoform, SET beta isoform, and the ratio of SET alpha to SET beta isoform mRNA are shown for 5 CLL patients in FIG. 22. These data further verified that the isoforms could be differentially detected in biological samples from subjects, and the ratio could be determined from the quantitative PCR measurements.

Marco, J. Jorda, and A. Durantez, *A sustained activation of PI3K/NF-kappaB pathway is critical for the survival of chronic lymphocytic leukemia B cells*. Leukemia, 2004. 18, 1391-400.

Longo, P. G., L. Laurenti, S. Gobessi, S. Sica, G. Leone, and D. G. Efremov, *The Akt/Mcl-1 pathway plays a prominent role in mediating antiapoptotic signals downstream of the B-cell receptor in chronic lymphocytic leukemia B cells*. Blood, 2008. 111, 846-55.

TABLE 7

SET alpha isomer (a), SET beta isomer (b), SET common (c) and ratios of SET alpha isomer to SET beta isomer in biological samples from CLL patients.

| TAF-1beta | TAF-1 common | a/b | a + b | c/a + b | c * 1.5 | c − a | c − a/b | | b/2 | a + b/2 | c/a + b/2 |
|---|---|---|---|---|---|---|---|---|---|---|---|
| 744,654 | 315,993 | 0.64 | 1,221,905 | 3.86687 | 473,990 | −161,257 | −0.2165534 | | 372326.925 | 849,578 | 0.37194179 |
| 51,489 | 47,369 | 0.22 | 62,571 | 1.32094 | 71,053 | 36,287 | 0.70474145 | 1.4189601 | 25744.64 | 36,827 | 1.28625997 |
| 92,405 | 53,824 | 0.19 | 110,211 | 2.04761 | 80,736 | 36,019 | 0.38979059 | 2.56548012 | 46202.655 | 64,008 | 0.84089641 |
| 119,972 | 74,739 | 0.25 | 149,891 | 2.00551 | 112,109 | 44,821 | 0.3735935 | 2.67670607 | 59985.96 | 89,905 | 0.83131853 |
| 85,784 | 67,638 | 0.19 | 101,711 | 1.50376 | 101,457 | 51,710 | 0.60279843 | 1.65892934 | 42891.95 | 58,819 | 1.149924 |
| 140,542 | 115,561 | 0.16 | 162,715 | 1.40804 | 173,342 | 93,388 | 0.66448791 | 1.50491827 | 70271.015 | 92,444 | 1.25007025 |
| 42,959 | 32,222 | 0.17 | 50,063 | 1.5537 | 48,333 | 25,117 | 0.58468638 | 1.71031861 | 21479.25 | 28,584 | 1.12727409 |
| 110,916 | 96,684 | 0.10 | 121,815 | 1.25994 | 145,026 | 85,784 | 0.77341766 | 1.29296246 | 55457.875 | 66,357 | 1.45701535 |
| 73,601 | 49,754 | 0.16 | 85,325 | 1.71496 | 74,630 | 38,030 | 0.51669651 | 1.9353721 | 36800.665 | 48,525 | 1.02532493 |
| 89,660 | 89,838 | 0.17 | 104,772 | 1.16623 | 134,757 | 74,727 | 0.83344167 | 1.19984402 | 44830.12 | 59,942 | 1.49876054 |
| 43,864 | 43,668 | 0.15 | 50,579 | 1.15826 | 65,502 | 36,954 | 0.84245175 | 1.1870116 | 21932.17 | 28,647 | 1.52436551 |
| 107,788 | 121,161 | 0.16 | 125,419 | 1.03514 | 181,741 | 103,530 | 0.96049748 | 1.04112715 | 53894.025 | 71,525 | 1.69397059 |
| 156,974 | 114,128 | 0.10 | 172,192 | 1.50876 | 171,192 | 98,910 | 0.63010338 | 1.58704116 | 78487.16 | 93,705 | 1.21794808 |
| 122,837 | 109,166 | 0.21 | 148,031 | 1.35602 | 163,749 | 83,972 | 0.68360181 | 1.46283989 | 61418.525 | 86,613 | 1.26038993 |
| 100,772 | 86,531 | 0.12 | 112,907 | 1.30481 | 129,797 | 74,397 | 0.73826466 | 1.35452779 | 50386.07 | 62,521 | 1.38403991 |
| 80,370 | 65,238 | 0.13 | 90,438 | 1.38628 | 97,856 | 55,170 | 0.68645247 | 1.45676511 | 40185.135 | 50,252 | 1.29819954 |
| 85,568 | 87,247 | 0.12 | 96,175 | 1.10233 | 130,871 | 76,640 | 0.89566079 | 1.11649411 | 42784.06 | 53,391 | 1.63411046 |
| 92,537 | 40,895 | 0.34 | 123,728 | 3.02552 | 61,342 | 9,704 | 0.10486371 | 9.53618708 | 46268.34 | 77,459 | 0.52795014 |
| 206,784 | 120,894 | 0.08 | 224,351 | 1.85576 | 181,341 | 103,327 | 0.49968692 | 2.00125311 | 103392.06 | 120,959 | 0.99946478 |
| 156,211 | 113,864 | 0.14 | 177,419 | 1.55817 | 170,796 | 92,656 | 0.59314371 | 1.68593207 | 78105.49 | 99,314 | 1.14650595 |
| 51,978 | 47,301 | 0.17 | 60,968 | 1.28895 | 70,951 | 38,311 | 0.73705392 | 1.35675283 | 25989.15 | 34,979 | 1.35226019 |
| 12,112 | 9,595 | 0.14 | 13,772 | 1.43528 | 14,392 | 7,936 | 0.6551799 | 1.52629835 | 6056.1 | 7,715 | 1.24361246 |
| 313,035 | 125,475 | 0.07 | 333,911 | 2.66118 | 188,212 | 104,599 | 0.33414505 | 2.99271227 | 156517.505 | 177,393 | 0.70732602 |
| 129,018 | 119,520 | 0.13 | 145,932 | 1.22099 | 179,279 | 102,606 | 0.79528264 | 1.2574146 | 64509.135 | 81,423 | 1.46788942 |
| 161,767 | 127,058 | 0.13 | 183,598 | 1.445 | 190,587 | 105,226 | 0.65048192 | 1.53732174 | 80883.37 | 102,715 | 1.23699562 |
| Avg | | 0.16 | | 1.55513 | | | 0.63543851 | 1.96096541 | | | 1.21507803 |

All literature publications discussed and cited herein are incorporated herein by reference in their entireties. It is understood that the disclosed invention is not limited to the particular methodology, protocols and materials described as these can vary. It is also understood that the terminology used herein is for the purposes of describing particular embodiments only and is not intended to limit the scope of the present invention which will be limited only by the appended claims.

Those skilled in the art will recognize, or be able to ascertain using no more than routine experimentation, many equivalents to the specific embodiments of the invention described herein. Such equivalents are intended to be encompassed by the following claims.

REFERENCES

Rozman, C. and E. Montserrat, *Chronic lymphocytic leukemia*. N Engl J Med, 1995. 333, 1052-7.

Cordone, I., E. Matutes, and D. Catovsky, *Monoclonal antibody Ki-67 identifies B and T cells in cycle in chronic lymphocytic leukemia: correlation with disease activity*. Leukemia, 1992. 6, 902-6.

Caligaris-Cappio, F. and T. J. Hamblin, *B-cell chronic lymphocytic leukemia: a bird of a different feather*. J Clin Oncol, 1999. 17, 399-408.

Cuni, S., P. Perez-Aciego, G. Perez-Chacon, J. A. Vargas, A. Sanchez, F. M. Martin-Saavedra, S. Ballester, J. Garcia- Li, M., A. Makkinje, and Z. Damuni, *The myeloid leukemia-associated protein SET is a potent inhibitor of protein phosphatase 2A*. J Biol Chem, 1996. 271, 11059-62.

Adachi, Y., G. N. Pavlakis, and T. D. Copeland, *Identification and characterization of SET, a nuclear phosphoprotein encoded by the translocation breakpoint in acute undifferentiated leukemia*. Journal of Biological Chemistry, 1994. 269, 2258-2262.

Neviani, P., R. Santhanam, R. Trotta, M. Notari, B. W. Blaser, S. Liu, H. Mao, J. S. Chang, A. Galietta, A. Uttam, D. C. Roy, M. Valtieri, R. Bruner-Klisovic, M. A. Caligiuri, C. D. Bloomfield, G. Marcucci, and D. Perrotti, *The tumor suppressor PP2A is functionally inactivated in blast crisis CML through the inhibitory activity of the BCR/ABL-regulated SET protein*. Cancer Cell, 2005. 8, 355-68.

Janssens, V., J. Goris, and C. Van Hoof, *PP2A: the expected tumor suppressor*. Curr Opin Genet Dev, 2005. 15, 34-41.

Eichhorn, P. J., M. P. Creyghton, and R. Bernards, *Protein phosphatase 2A regulatory subunits and cancer*. Biochim Biophys Acta, 2009. 1795, 1-15.

Katoh, F., D. J. Fitzgerald, L. Giroldi, H. Fujiki, T. Sugimura, and H. Yamasaki, *Okadaic acid and phorbol esters: comparative effects of these tumor promoters on cell transformation, intercellular communication and differentiation in vitro*. Jpn J Cancer Res, 1990. 81, 590-7.

Schonthal, A. H., *Role of serine/threonine protein phosphatase 2A in cancer*. Cancer Lett, 2001. 170, 1-13.

Chen, W., R. Possemato, K. T. Campbell, C. A. Plattner, D. C. Pallas, and W. C. Hahn, *Identification of specific PP2A complexes involved in human cell transformation.* Cancer Cell, 2004. 5, 127-36.

Rangarajan, A., S. J. Hong, A. Gifford, and R. A. Weinberg, *Species-and cell type-specific requirements for cellular transformation.* Cancer Cell, 2004. 6, 171-83.

Christensen, D. J., Y. Chen, J. Oddo, K. M. Matta, J. Neil, E. D. Davis, A. D. Volkheimer, M. C. Lanasa, D. R. Friedman, B. K. Goodman, J. P. Gockerman, L. F. Diehl, C. M. de Castro, J. O. Moore, M. P. Vitek, and J. B. Weinberg, *SET oncoprotein overexpression in B-cell chronic lymphocytic leukemia and non-Hodgkin lymphoma: a predictor of aggressive disease and a new treatment target.* Blood, 2011. 118, 4150-8.

Sablina, A. A. and W. C. Hahn, *SV40 small T antigen and PP2A phosphatase in cell transformation.* Cancer Metastasis Rev, 2008. 27, 137-46.

Kalla, C., M. O. Scheuermann, I. Kube, M. Schlotter, D. Mertens, H. Dohner, S. Stilgenbauer, and P. Lichter, *Analysis of 11q22-q23 deletion target genes in B-cell chronic lymphocytic leukaemia: evidence for a pathogenic role of NPAT, CUL5, and PPP2R1B.* Eur J Cancer, 2007. 43, 1328-35.

Suzuki, K. and K. Takahashi, *Reduced expression of the regulatory A subunit of serine/threonine protein phosphatase 2A expression in human breast cancer MCF-7 cells.* Int J Oncol, 2003. 23, 1263-8.

Suzuki, K. and K. Takahashi, *Induction of E-cadherin endocytosis by loss of protein phosphatase 2A expression in human breast cancers.* Biochem Biophys Res Commun, 2006. 349, 255-60.

Woodland, R. T., C. J. Fox, M. R. Schmidt, P. S. Hammerman, J. T. Opferman, S. J. Korsmeyer, D. M. Hilbert, and C. B. Thompson, *Multiple signaling pathways promote B lymphocyte stimulator dependent B-cell growth and survival.* Blood, 2008. 111, 750-60.

Boeshore, K. L., R. C. Schreiber, S. A. Vaccariello, H. H. Sachs, R. Salazar, J. Lee, R. R. Ratan, P. Leahy, and R. E. Zigmond, *Novel changes in gene expression following axotomy of a sympathetic ganglion: a microarray analysis.* J Neurobiol, 2004. 59, 216-35.

Petlickovski, A., L. Laurenti, X. Li, S. Marietti, P. Chiusolo, S. Sica, G. Leone, and D. G. Efremov, *Sustained signaling through the B-cell receptor induces Mcl-1 and promotes survival of chronic lymphocytic leukemia B cells.* Blood, 2005. 105, 4820-7.

Cardone, M. H., N. Roy, H. R. Stennicke, G. S. Salvesen, T. F. Franke, E. Stanbridge, S. Frisch, and J. C. Reed, *Regulation of cell death protease caspase-9 by phosphorylation.* Science, 1998. 282, 1318-21.

Alvarado-Kristensson, M., F. Melander, K. Leandersson, L. Ronnstrand, C. Wernstedt, and T. Andersson, *p38-MAPK signals survival by phosphorylation of caspase-8 and caspase-3 in human neutrophils.* J Exp Med, 2004. 199, 449-58.

Aggarwal, B. B., *Nuclear factor-kappaB: the enemy within.* Cancer Cell, 2004. 6, 203-8.

Granziero, L., P. Ghia, P. Circosta, D. Gottardi, G. Strola, M. Geuna, L. Montagna, P. Piccoli, M. Chilosi, and F. Caligaris-Cappio, *Survivin is expressed on CD40 stimulation and interfaces proliferation and apoptosis in B-cell chronic lymphocytic leukemia.* Blood, 2001. 97, 2777-83.

Aron, J. L., M. R. Parthun, G. Marcucci, S. Kitada, A. P. Mone, M. E. Davis, T. Shen, T. Murphy, J. Wickham, C. Kanakry, D. M. Lucas, J. C. Reed, M. R. Greyer, and J. C. Byrd, *Depsipeptide (FR901228) induces histone acetylation and inhibition of histone deacetylase in chronic lymphocytic leukemia cells concurrent with activation of caspase 8-mediated apoptosis and down-regulation of c-FLIP protein.* Blood, 2003. 102, 652-8.

Schimmer, A. D., I. Munk-Pedersen, M. D. Minden, and J. C. Reed, *Bcl-2 and apoptosis in chronic lymphocytic leukemia.* Curr Treat Options Oncol, 2003. 4, 211-8.

Hewamana, S., S. Alghazal, T. T. Lin, M. Clement, C. Jenkins, M. L. Guzman, C. T. Jordan, S. Neelakantan, P. A. Crooks, A. K. Burnett, G. Pratt, C. Fegan, C. Rowntree, P. Brennan, and C. Pepper, *The NF-kappaB subunit Rel A is associated with in vitro survival and clinical disease progression in chronic lymphocytic leukemia and represents a promising therapeutic target.* Blood, 2008. 111, 4681-9.

Damle, R. N., T. Wasil, F. Fais, F. Ghiotto, A. Valetto, S. L. Allen, A. Buchbinder, D. Budman, K. Dittmar, J. Kolitz, S. M. Lichtman, P. Schulman, V. P. Vinciguerra, K. R. Rai, M. Ferrarini, and N. Chiorazzi, *Ig V gene mutation status and CD38 expression as novel prognostic indicators in chronic lymphocytic leukemia.* Blood, 1999. 94, 1840-7.

Hamblin, T. J., Z. Davis, A. Gardiner, D. G. Oscier, and F. K. Stevenson, *Unmutated Ig V(H) genes are associated with a more aggressive form of chronic lymphocytic leukemia.* Blood, 1999. 94, 1848-54.

Ibrahim, S., M. Keating, K. A. Do, S. O'Brien, Y. O. Huh, I. Jilani, S. Lerner, H. M. Kantarjian, and M. Albitar, *CD38 expression as an important prognostic factor in B-cell chronic lymphocytic leukemia.* Blood, 2001. 98, 181-6.

Rassenti, L. Z., L. Huynh, T. L. Toy, L. Chen, M. J. Keating, J. G. Gribben, D. S. Neuberg, I. W. Flinn, K. R. Rai, J. C. Byrd, N. E. Kay, A. Greaves, A. Weiss, and T. J. Kipps, *ZAP-70 compared with immunoglobulin heavy-chain gene mutation status as a predictor of disease progression in chronic lymphocytic leukemia.* N Engl J Med, 2004. 351, 893-901.

Nelson, P. N., G. M. Reynolds, E. E. Waldron, E. Ward, K. Giannopoulos, and P. G. Murray, *Monoclonal antibodies.* Molecular pathology: MP, 2000. 53, 111-7.

Kyte, J. and R. F. Doolittle, *A simple method for displaying the hydropathic character of a protein.* Journal of molecular biology, 1982. 157, 105-32.

Tam, J. P., *High-density multiple antigen-peptide system for preparation of antipeptide antibodies.* Methods in Enzymology, 1989. 168, 7-15.

Hoane, M. R., J. L. Pierce, M. A. Holland, N. D. Birky, T. Dang, M. P. Vitek, and S. E. McKenna, *The novel apolipoprotein E-based peptide COG1410 improves sensorimotor performance and reduces injury magnitude following cortical contusion injury.* J Neurotrauma, 2007. 24, 1108-18.

Li M, Makkinje A, Damuni Z. *The myeloid leukemia-associated protein SET is a potent inhibitor of protein phosphatase 2A.* J Biol Chem. 1996; 271:11059-11062.

Adachi Y, Pavlakis G N, Copeland T D. *Identification and characterization of SET, a nuclear phosphoprotein encoded by the translocation break point in acute undifferentiated leukemia.* Journal of Biological Chemistry. 1994; 269:2258-2262.

Neviani P, Santhanam R, Trotta R, et al. *The tumor suppressor PP2A is functionally inactivated in blast crisis CML through the inhibitory activity of the BCR/ABL-regulated SET protein.* Cancer Cell. 2005; 8:355-368.

Janssens V, Goris J, Van Hoof C. *PP2A: the expected tumor suppressor.* Curr Opin Genet Dev. 2005; 15:34-41.

Eichhorn P J, Creyghton M P, Bernards R. *Protein phosphatase 2A regulatory subunits and cancer.* Biochim Biophys Acta. 2009; 1795:1-15.

Katoh F, Fitzgerald D J, Giroldi L, Fujiki H, Sugimura T, Yamasaki H. Okadaic acid and phorbol esters: comparative effects of these tumor promoters on cell transformation, intercellular communication and differentiation in vitro. Jpn J Cancer Res. 1990; 81:590-597.

Schonthal A H. Role of serine/threonine protein phosphatase 2A in cancer. Cancer Lett. 2001; 170:1-13.

Chen W, Possemato R, Campbell K T, Plattner C A, Pallas D C, Hahn W C. Identification of specific PP2A complexes involved in human cell transformation. Cancer Cell. 2004; 5:127-136.

Rangarajan A, Hong S J, Gifford A, Weinberg R A. Species- and cell type-specific requirements for cellular transformation. Cancer Cell. 2004; 6:171-183.

Ishibe N, Sgambati M T, Fontaine L, et al. Clinical characteristics of familial B-CLL in the National Cancer Institute Familial Registry. Leuk Lymphoma. 2001; 42:99-108.

Rozman C, Montserrat E. Chronic lymphocytic leukemia. N Engl J Med. 1995; 333:1052-1057.

Cordone I, Matutes E, Catovsky D. Monoclonal antibody Ki-67 identifies B and T cells in cycle in chronic lymphocytic leukemia: correlation with disease activity. Leukemia. 1992; 6:902-906.

Caligaris-Cappio F, Hamblin T J. B-cell chronic lymphocytic leukemia: a bird of a different feather. J Clin Oncol. 1999; 17:399-408.

Cuni S, Perez-Aciego P, Perez-Chacon G, et al. A sustained activation of PI3K/NF-kappaB pathway is critical for the survival of chronic lymphocytic leukemia B cells. Leukemia. 2004; 18:1391-1400.

Longo P G, Laurenti L, Gobessi S, Sica S, Leone G, Efremov D G. The Akt/Mcl-1 pathway plays a prominent role in mediating antiapoptotic signals downstream of the B-cell receptor in chronic lymphocytic leukemia B cells. Blood. 2008; 111:846-855.

Hallek M, Cheson B D, Catovsky D, et al. Guidelines for the diagnosis and treatment of chronic lymphocytic leukemia: a report from the International Workshop on Chronic Lymphocytic Leukemia updating the National Cancer Institute-Working Group 1996 guidelines. Blood. 2008; 111:5446-5456.

Weinberg J B, Volkheimer A D, Chen Y, et al. Clinical and molecular predictors of disease severity and survival in chronic lymphocytic leukemia. Am J Hematol. 2007; 82:1063-1070.

Hoane M R, Pierce J L, Holland M A, et al. The novel apolipoprotein E-based peptide COG 1410 improves sensorimotor performance and reduces injury magnitude following cortical contusion injury. J Neurotrauma. 2007; 24:1108-1118.

Romero-Calvo I, Ocon B, Martinez-Moya P, et al. Reversible Ponceau staining as a loading control alternative to actin in Western blots. Anal Biochem. 2010; 401:318-320.

Levesque M C, Ghosh D K, Beasley B E, et al. CLL cell apoptosis induced by nitric oxide synthase inhibitors: correlation with lipid solubility and NOS1 dissociation constant. Leuk Res. 2008; 32:1061-1070.

Levesque M C, O'Loughlin C W, Weinberg J B. Use of serum-free media to minimize apoptosis of chronic lymphocytic leukemia cells during in vitro culture. Leukemia. 2001; 15:1305-1307.

Levesque M C, Misukonis M A, O'Loughlin C W, et al. IL-4 and interferon gamma regulate expression of inducible nitric oxide synthase in chronic lymphocytic leukemia cells. Leukemia. 2003; 17:442-450.

Schliemann C, Palumbo A, Zuberbuhler K, et al. Complete eradication of human B-cell lymphoma xenografts using rituximab in combination with the immunocytokine L19-IL2. Blood. 2009; 113:2275-2283.

Christensen D J, Ohkubo N, Oddo J, et al. Apolipoprotein E and Peptide Mimetics Modulate Inflammation by Binding the SET Protein and Activating Protein Phosphatase 2A. J Immunol. 2011; 186:2535-2542.

Li F Q, Sempowski G D, McKenna S E, Laskowitz D T, Colton C A, Vitek M P. Apolipoprotein E-derived peptides ameliorate clinical disability and inflammatory infiltrates into the spinal cord in a murine model of multiple sclerosis. J Pharmacol Exp Ther. 2006; 318:956-965.

Singh K, Chaturvedi R, Asim M, et al. The apolipoprotein E-mimetic peptide COG 112 inhibits the inflammatory response to citrobacter rodentium in colonic epithelial cells by preventing NF-kappa B activation. J Biol Chem. 2008; 283:16752-16761.

Neviani P, Santhanam R, Oaks J J, et al. FTY720, a new alternative for treating blast crisis chronic myelogenous leukemia and Philadelphia chromosome-positive acute lymphocytic leukemia. J Clin Invest. 2007; 117:2408-2421.

Johnson A J, Lucas D M, Muthusamy N, et al. Characterization of the TCL-1 transgenic mouse as a preclinical drug development tool for human chronic lymphocytic leukemia. Blood. 2006; 108:1334-1338.

Asaka M N, Murano K, Nagata K. Sp1-mediated transcription regulation of TAF-Ialpha gene encoding a histone chaperone. Biochem Biophys Res Commun. 2008; 376:665-670.

Rosenwald A, Alizadeh A A, Widhopf G, et al. Relation of gene expression phenotype to immunoglobulin mutation genotype in B cell chronic lymphocytic leukemia. J Exp Med. 2001; 194:1639-1647.

Dohner H, Stilgenbauer S, Benner A, et al. Genomic aberrations and survival in chronic lymphocytic leukemia. N Engl J Med. 2000; 343:1910-1916.

Kalla C, Scheuermann M O, Kube I, et al. Analysis of 11q22-q23 deletion target genes in B-cell chronic lymphocytic leukaemia: evidence for a pathogenic role of NPAT, CUL5, and PPP2R1B. Eur J Cancer. 2007; 43:1328-1335.

Ivaska J, Nissinen L, Immonen N, Eriksson J E, Kahari V M, Heino J. Integrin alpha 2 beta 1 promotes activation of protein phosphatase 2A and dephosphorylation of Akt and glycogen synthase kinase 3 beta. Mol Cell Biol. 2002; 22:1352-1359.

Kuo Y C, Huang K Y, Yang C H, Yang Y S, Lee W Y, Chiang C W. Regulation of phosphorylation of Thr-308 of Akt, cell proliferation, and survival by the B55alpha regulatory subunit targeting of the protein phosphatase 2A holoenzyme to Akt. J Biol Chem. 2008; 283:1882-1892.

Liu Q, Hofmann P A. Protein phosphatase 2A-mediated cross-talk between p38 MAPK and ERK in apoptosis of cardiac myocytes. Am J Physiol Heart Circ Physiol. 2004; 286:H2204-2212.

Herling M, Patel K A, Khalili J, et al. TCL1 shows a regulated expression pattern in chronic lymphocytic leukemia that correlates with molecular subtypes and proliferative state. Leukemia. 2006; 20:280-285.

Chiang C W, Kanies C, Kim K W, et al. Protein phosphatase 2A dephosphorylation of phosphoserine 112 plays the gatekeeper role for BAD-mediated apoptosis. Mol Cell Biol. 2003; 23:6350-6362.

Alvarado-Kristensson M, Andersson T. Protein phosphatase 2A regulates apoptosis in neutrophils by dephosphorylating both p38 MAPK and its substrate caspase 3. J Biol Chem. 2005; 280:6238-6244.

Buggins A G, Pepper C J. The role of Bcl-2 family proteins in chronic lymphocytic leukaemia. Leuk Res. 2010; 34:837-842.

Kitada S, Andersen J, Akar S, et al. Expression of apoptosis-regulating proteins in chronic lymphocytic leukemia: correlations with In vitro and In vivo chemoresponses. Blood. 1998; 91:3379-3389.

Stevenson F K, Caligaris-Cappio F. Chronic lymphocytic leukemia: revelations from the B-cell receptor. Blood. 2004; 103:4389-4395.

Pepper C, Lin T T, Pratt G, et al. Mcl-1 expression has in vitro and in vivo significance in chronic lymphocytic leukemia and is associated with other poor prognostic markers. Blood. 2008; 112:3807-3817.

Cho-Vega J H, Rassidakis G Z, Admirand J H, et al. MCL-1 expression in B-cell non-Hodgkin's lymphomas. Hum Pathol. 2004; 35:1095-1100.

Gandhi V, Balakrishnan K, Chen L S. Mcl-1: the 1 in CLL. Blood. 2008; 112:3538-3540.

Maurer U, Charvet C, Wagman A S, Dejardin E, Green D R. Glycogen synthase kinase-3 regulates mitochondrial outer membrane permeabilization and apoptosis by destabilization of MCL-1. Mol Cell. 2006; 21:749-760.

Ding Q, He X, Hsu J M, et al. Degradation of Mcl-1 by beta-TrCP mediates glycogen synthase kinase 3-induced tumor suppression and chemosensitization. Mol Cell Biol. 2007; 27:4006-4017.

Kim L, Kimmel A R. GSK3, a master switch regulating cell-fate specification and tumorigenesis. Curr Opin Genet Dev. 2000; 10:508-514.

Ding Q, He X, Xia W, et al. Myeloid cell leukemia-1 inversely correlates with glycogen synthase kinase-3beta activity and associates with poor prognosis in human breast cancer. Cancer Res. 2007; 67:4564-4571.

Switzer C H, Cheng R Y, Vitek T M, Christensen D J, Wink D A, Vitek M P. Targeting SET/I(2)PP2A oncoprotein functions as a multi-pathway strategy for cancer therapy. Oncogene. 2011; 30:2504-2513.

Liu Q, Zhao X, Frissora F, et al. FTY720 demonstrates promising preclinical activity for chronic lymphocytic leukemia and lymphoblastic leukemia/lymphoma. Blood. 2008; 111:275-284.

The invention claimed is:

1. A method of predicting or assessing the level of severity of cancer or cancer progression in a patient diagnosed with chronic lymphocytic leukemia or B-cell non-Hodgkin's lymphoma comprising determining the ratio of SET alpha isoform to SET beta isoform in B lymphocytes isolated from the patient and comparing the ratio of SET alpha isoform to SET beta isoform to the ratio in a control sample or a standard value,
   wherein an increase in the ratio of SET alpha isoform to SET beta isoform relative to the ratio in the control sample or standard value is indicative of a more severe form of cancer or later stage of cancer progression in the patient.

2. The method of claim 1, wherein the ratio of SET alpha isoform to SET beta isoform is determined by
   contacting the B lymphocytes or extracts thereof with a SET alpha isoform-specific antibody and a SET beta isoform-specific antibody;
   measuring the level of SET protein detected by each antibody; and
   calculating the ratio of SET alpha isoform protein to SET beta isoform protein in the B lymphocytes.

3. The method of claim 1, wherein the ratio of SET alpha isoform to SET beta isoform is determined by
   contacting the B lymphocytes or extracts thereof with (i) a SET-specific antibody and a SET alpha isoform-specific antibody or fii) a SET-specific antibody and a SET beta isoform-specific antibody;
   measuring the level of SET protein detected by each antibody;
   subtracting the level of isoform-specific SET protein from the level of total SET protein; and
   calculating the ratio of SET alpha isoform protein to SET beta isoform protein in the B lymphocytes.

4. The method of claim 2 or 3, wherein the level of SET protein is measured by imaging, immunoblotting, enzyme-linked immunoassay, or by flow cytometry.

5. The method of claim 1, wherein the ratio of SET alpha isoform to SET beta isoform is determined by
   extracting RNA from the B lymphocytes;
   quantifying SET mRNA from the extracted RNA using a nucleic acid probe targeting alpha isoform SET mRNA and a nucleic acid probe targeting beta isoform SET mRNA, and calculating the ratio of SET alpha isoform mRNA to SET beta isoform mRNA in the B lymphocytes.

6. The method of claim 1, wherein the ratio of SET alpha isoform to SET beta isoform is determined by extracting RNA from the B lymphocytes;

quantifying SET mRNA from the extracted RNA using (i) a nucleic acid probe targeting alpha isoform SET mRNA and a nucleic acid probe targeting SET mRNA, or (ii) a nucleic acid probe targeting beta isoform SET mRNA and a nucleic acid probe targeting SET mRNA;

subtracting the level of isoform-specific SET mRNA from the level of total SET mRNA; and calculating the ratio of SET alpha isoform mRNA to SET beta isoform mRNA in the B lymphocytes.

7. The method of claim 5, wherein the nucleic acid probe targeting alpha isoform SET mRNA is according to SEQ ID NO: 7, and the nucleic acid probe targeting beta isoform SET mRNA is according to SEQ ID NO: 10.

8. The method of claim 6, wherein the nucleic acid probe targeting alpha isoform SET mRNA is according to SEQ ID NO: 7, the nucleic acid probe targeting beta isoform SET mRNA is according to SEQ ID NO: 10, and the nucleic acid probe targeting SET mRNA is according to SEQ ID NO: 13.

9. The method of claim 1, further comprising determining one or more prognostic factors in the patient, wherein the prognostic factors are IGVH mutation, CD38 expression, ZAP70 expression, or combinations thereof.

10. The method of claim 1, wherein the B lymphocytes are isolated from a blood sample from the patient.

11. The method of claim 1, wherein the B lymphocytes are CD19+/CD5+ B lymphocytes.

12. The method of claim 1, further comprising identifying a patient with an increase in the ratio of SET alpha isoform to SET beta isoform relative to the ratio in a control sample or a standard value; and treating the identified patient with an aggressive treatment regimen for chronic lymphocytic leukemia or B-cell non-Hodgkin's lymphoma.

13. The method of claim 12, further comprising determining one or more prognostic factors in the patient, wherein the prognostic factors are IGVH mutation, CD38 expression, ZAP70 expression, or combinations thereof.

14. The method of claim 2 or 3, wherein the SET alpha isoform-specific antibody recognizes an antigen having the sequence of SEQ ID NO: 2.

15. The method of claim 2 or 3, wherein the SET beta isoform-specific antibody recognizes an antigen having the sequence of SEQ ID NO: 4.

16. The method of claim 5 or 6, wherein the SET mRNA is quantified by RT-PCR.

17. The method of claim 5 or 6, wherein quantifying comprises amplifying SET alpha isoform mRNA using a pair of nucleic acid primers, wherein one primer has a sequence of SEQ ID NO: 5 and the other primer has a sequence of SEQ ID NO: 6.

18. The method of claim 5 or 6, wherein quantifying comprises amplifying SET beta isoform mRNA using a pair of nucleic acid primers, wherein one primer has a sequence of SEQ ID NO: 8 and the other primer has a sequence of SEQ ID NO: 9.

19. The method of claim 6, wherein quantifying comprises amplifying SET mRNA using a pair of nucleic acid primers, wherein one primer has a sequence of SEQ ID NO: 11 and the other primer has a sequence of SEQ ID NO: 12.

* * * * *